(12) United States Patent
Hughes et al.

(10) Patent No.: US 10,500,109 B2
(45) Date of Patent: Dec. 10, 2019

(54) ABSORBENT ARTICLE HAVING FUNCTIONAL ENHANCEMENT INDICATORS

(71) Applicant: The Procter & Gamble Company, Cincinnati, OH (US)

(72) Inventors: Jeanne Marie Hughes, Deerfield Township, OH (US); Ronald Bosman Visscher, Glendale, OH (US); Peter Charles Mason, Jr., Maineville, OH (US); Folke Schlueter, Geneva (CH); Emma Somma, Frankfurt am Main (DE); Giovanni Carlucci, Chieti (IT); Paul Thomas Weisman, Sharonville, OH (US)

(73) Assignee: The Procter & Gamble Company, Cincinnati, OH (US)

(*) Notice: Subject to any disclaimer, the term of this patent is extended or adjusted under 35 U.S.C. 154(b) by 299 days.

(21) Appl. No.: 14/276,183

(22) Filed: May 13, 2014

(65) Prior Publication Data

US 2014/0257224 A1    Sep. 11, 2014

Related U.S. Application Data

(63) Continuation of application No. 13/668,789, filed on Nov. 5, 2012, now Pat. No. 8,766,033, which is a (Continued)

(51) Int. Cl.
*A61F 13/472* (2006.01)
*A61F 13/15* (2006.01)
(Continued)

(52) U.S. Cl.
CPC ............ *A61F 13/84* (2013.01); *A61F 13/472* (2013.01); *A61F 13/47254* (2013.01); (Continued)

(58) Field of Classification Search
CPC .......... A61F 13/15; A61F 13/45; A61F 13/47; A61F 13/472; A61F 13/505; A61F 13/56; (Continued)

(56) References Cited

U.S. PATENT DOCUMENTS 4,662,875 A     5/1987  Hirotsu et al.
4,673,403 A  *  6/1987  Lassen ............. A61F 13/47227
                                                     604/361

(Continued)

FOREIGN PATENT DOCUMENTS

EP    0526225 A1 *  2/1993  ............. A61F 13/45
EP    1208823 A1    5/2002
(Continued)

OTHER PUBLICATIONS

PCT International Search Report dated Apr. 5, 2006.

*Primary Examiner* — Peter S Vasat
(74) *Attorney, Agent, or Firm* — Andrew J. Hagerty; George H. Leal

(57) ABSTRACT

An absorbent article with a body-facing surface, a first end region a second end region, a topsheet, a backsheet, and an absorbent core disposed between the topsheet and the backsheet is described. The absorbent article can be asymmetric about the transverse centerline, and can have a first functional enhancement indicator visible from the body-facing surface and a second functional enhancement indicator visible from the body-facing surface. The first functional enhancement indicator can provide visually-perceptible indication of the first end region, and the second functional enhancement indicator can provide visually-perceptible indication of a region of fluid entry in the absorbent article.

6 Claims, 15 Drawing Sheets

Related U.S. Application Data continuation of application No. 11/013,268, filed on Dec. 15, 2004, now Pat. No. 8,304,597.

(51) Int. Cl.
*A61F 13/84* (2006.01)
*A61F 13/551* (2006.01)

(52) U.S. Cl.
CPC .. *A61F 13/55145* (2013.01); *A61F 13/15203* (2013.01); *A61F 2013/8497* (2013.01)

(58) Field of Classification Search
CPC .......... A61F 13/58; A61F 13/60; A61F 13/74; A61F 13/76; A61F 13/80; A61F 13/82; A61F 2013/8497; A61F 13/51394; A61F 2013/51377; A61L 15/16; A61L 15/58
See application file for complete search history.

(56) References Cited

U.S. PATENT DOCUMENTS

| | | | |
|---|---|---|---|
| 5,035,691 A | 7/1991 | Zimmel et al. | |
| 5,300,054 A | 4/1994 | Feist et al. | |
| 5,304,161 A | 4/1994 | Noel et al. | |
| 5,342,861 A | 8/1994 | Raykovitz | |
| 5,401,267 A | 3/1995 | Couture-Dorschner et al. | |
| 5,439,458 A | 8/1995 | Noel et al. | |
| 5,503,076 A | 4/1996 | Yeo | |
| 5,688,259 A * | 11/1997 | Osborn, III | A61F 13/4704 604/378 |
| 5,713,886 A * | 2/1998 | Sturino | A61F 13/47254 604/385.04 |
| 6,297,424 B1 | 10/2001 | Olson et al. | |
| 6,307,119 B1 | 10/2001 | Cammarota et al. | |
| 6,568,530 B2 | 5/2003 | Takahashi et al. | |
| 6,596,918 B1 | 7/2003 | Wehrle et al. | |
| 6,601,705 B2 | 8/2003 | Molina et al. | |
| 6,617,488 B1 | 9/2003 | Springer et al. | |
| 6,651,551 B1 | 11/2003 | Castellanos | |
| 6,681,934 B2 | 1/2004 | Kolterjohn et al. | |
| 6,710,221 B1 | 3/2004 | Pierce et al. | |
| 6,733,483 B2 | 5/2004 | Raufman et al. | |
| 6,763,944 B2 | 7/2004 | Ronn et al. | |
| 6,921,647 B2 | 7/2005 | Kritzman et al. | |
| 6,949,681 B2 | 9/2005 | Linsell | |
| 7,159,532 B2 | 1/2007 | Klofta et al. | |
| 7,322,472 B2 | 1/2008 | Swiecicki et al. | |
| 7,959,620 B2 | 6/2011 | Miura et al. | |
| 2001/0031954 A1 | 10/2001 | Jordan et al. | |
| 2002/0025752 A1 * | 2/2002 | Taniguchi | A61F 13/551 442/327 |
| 2003/0073966 A1 | 4/2003 | Sosalla et al. | |
| 2003/0078553 A1 * | 4/2003 | Wada | A61F 13/42 604/361 |
| 2003/0106825 A1 | 6/2003 | Molina et al. | |
| 2003/0109839 A1 * | 6/2003 | Costea | A61F 13/42 604/358 |
| 2003/0114809 A1 | 6/2003 | Gagliardi et al. | |
| 2003/0114848 A1 | 6/2003 | Cobb | |
| 2003/0130632 A1 | 7/2003 | Costea et al. | |
| 2003/0158532 A1 * | 8/2003 | Magee | A61F 13/495 604/385.01 |
| 2003/0187415 A1 | 10/2003 | Kudo et al. | |
| 2004/0102748 A1 | 5/2004 | Hirotsu | |
| 2004/0122386 A1 | 6/2004 | Mocadlo | |
| 2005/0209576 A1 | 9/2005 | Hirotsu | |
| 2005/0261653 A1 * | 11/2005 | Digiacomantonio | A61F 13/84 604/385.03 |

FOREIGN PATENT DOCUMENTS

| | | |
|---|---|---|
| JP | 2002360620 A | 12/2002 |
| JP | 2003230592 A | 8/2003 |

* cited by examiner

ABSORBENT ARTICLE HAVING FUNCTIONAL ENHANCEMENT INDICATORS

CROSS REFERENCE TO RELATED APPLICATIONS

This application is a continuation of application Ser. No. 13/668,789 filed on Nov. 5, 2012, which is a continuation of application Ser. No. 11/013,268, filed Dec. 15, 2004, each of which is incorporated herein by reference.

FIELD OF THE INVENTION

The present invention relates to disposable absorbent products, and more particularly to feminine hygiene articles intended to be worn in women's undergarments.

BACKGROUND

Absorbent articles, such as sanitary napkins, are used by women principally during their menstrual periods to receive and contain menses and other vaginal discharges to protect their garments from soiling. Other articles, such as incontinence pads are similarly worn for control of light urine incontinence. Sanitary napkins and incontinence pads typically have adhesive attachment means to temporarily adhere the device to the crotch region of the user's undergarment, normally her panty.

When placing an absorbent article in an undergarment, it is often critical that the article be positioned correctly with respect to the crotch portion thereof. Improper positioning of the absorbent article can result in bodily discharges coming into contact with the wearer's garments or undergarment, instead of entering the absorbent article. For example, if the absorbent article is placed too far toward the front of the undergarment, a rearward portion of the undergarment may not be covered by the absorbent article, resulting in fluid, such as menses, soiling the undergarment. The problem is made worse when the absorbent article is asymmetrically-shaped, such that it does not provide an inherent indication of proper placement. Further, if the product has what are commonly referred to as "wings" or "flaps" intended to wrap the edges of the wearer's undergarments in the crotch region and/or affix the article to the undergarment, misplacement of the article can result in poor folding and premature detachment.

Asymmetrically-shaped absorbent articles, such as absorbent articles that are narrow in the front and wide in the back, or otherwise are not symmetric about a transverse centerline such as "pear-shaped" sanitary napkins, are known in the art. Such articles are intended to be worn with the larger surface area region oriented to the back of the wearer. Sanitary napkins designed in this manner can be more effective in preventing soiling of the undergarments. Asymmetrically-shaped absorbent articles are also known for control of light urine incontinence. For example, U.S. Pat. No. 5,439,458 issued to Noel et al. discloses an absorbent article such as an adult incontinence pad having an improved shape. The shape is described as being symmetrical about its longitudinal centerline, but asymmetrical about its transverse centerline.

However, the problem with asymmetrically-shaped absorbent articles, particularly such articles for use as feminine hygiene articles, is that the asymmetric nature of the pad renders it difficult to place correctly in the user's undergarment. Specifically with respect to sanitary napkins and incontinence pads, it is confusing to the user which of the asymmetrically-shaped ends goes in the rear or in the front, respectively, with respect to the undergarment. For incontinence pads, for example, some users tend to intuitively place the larger surface area portion to the rear, as is desirable with a similarly-shaped sanitary napkin intended for menstrual use, when, in fact, the larger surface area portion is intended to be oriented to the front of her undergarment.

Other problems associated with feminine hygiene articles include effectively communicating a particular benefit of a particular article to the user. For example, an article such as sanitary napkin may have enhanced functionality in one portion, such as enhanced absorbency nearer one end or another. It would be beneficial for the user to have some way of knowing which portion of the article has the enhanced absorbency. Knowing this would facilitate proper orientation and placement of the article in her undergarment.

Accordingly, there remains an unaddressed need for an improved feminine hygiene article, such as a sanitary napkin or pantiliner that is designed to facilitate proper placement and positioning in a user's undergarment.

Further, there is an unaddressed need for a means for properly placing and positioning a feminine hygiene article in an undergarment when the absorbent article is not symmetric about a longitudinal and/or transverse centerline thereof.

Also, there is an unaddressed need for a feminine hygiene article, or an array of feminine hygiene articles, that effectively communicate to the user differences in functionality that may be present in various portions thereof. Such a need is unaddressed both for symmetrically- and asymmetrically-shaped articles.

Finally, there is an unaddressed need for an asymmetrically-shaped incontinence pad comprising means for facilitating proper orientation and/or placement.

SUMMARY OF THE INVENTION

Absorbent articles of the present invention can provide the consumer with functional enhancement indicators which provide visually-perceptible indications to the consumer. In one embodiment, an absorbent article has a body-facing surface, a first end region a second end region, a topsheet, a backsheet, an absorbent core disposed between the topsheet and the backsheet. The absorbent article is adapted for placement in an undergarment having a crotch portion disposed between the first end region and the second end region. The absorbent article has a longitudinal centerline and a transverse centerline. The centerlines are perpendicular to one another in the plane of the absorbent article when in a flat out configuration. The absorbent article is asymmetric about the transverse centerline.

The absorbent article further comprises a first functional enhancement indicator visible from the body-facing surface, wherein the first functional enhancement indicator provides visually-perceptible indication of the first end region. The absorbent article further comprises a second functional enhancement indicator visible from the body-facing surface, wherein the second functional enhancement indicator provides visually-perceptible indication of a region of fluid entry in the absorbent article.

In another embodiment, an absorbent article has a body-facing surface, a first end region a second end region, a topsheet, a backsheet, and an absorbent core disposed between the topsheet and the backsheet. The absorbent article being adapted for placement in an undergarment having a crotch portion disposed between the first end region and the second end region. The absorbent article has a longitudinal centerline and a transverse centerline. The centerlines are perpendicular to one another in the plane of the absorbent article when in a flat out configuration. The absorbent core is asymmetric about the transverse centerline, and the absorbent article further comprising a first functional enhancement indicator visible from the body-facing surface. The first functional enhancement indicator provides visually-perceptible indication of the first end region, and further comprising a second functional enhancement indicator visible from the body-facing surface, wherein the second functional enhancement indicator provides visually-perceptible indication of a region of fluid entry in the absorbent article.

In yet another embodiment, an absorbent article has a body-facing surface, a first end region a second end region, a topsheet, a backsheet, and an absorbent core disposed between the topsheet and the backsheet. The absorbent article is adapted for placement in an undergarment having a crotch portion disposed between the first end region and the second end region. The absorbent article has a longitudinal centerline and a transverse centerline. The centerlines are perpendicular to one another in the plane of the absorbent article when in a flat out configuration.

The absorbent article further comprises a first functional enhancement indicator visible from the body-facing surface, wherein the first functional enhancement indicator provides visually-perceptible indication of the first end region and bounds, at least in part, a fluid entry region of the absorbent article. The absorbent article further comprises a second functional enhancement indicator visible from the body-facing surface, wherein the second functional enhancement indicator provides visually-perceptible indication of the region of fluid entry in the absorbent article.

DETAILED DESCRIPTION OF THE INVENTION

As used herein, the term "absorbent article" refers to devices that absorb and contain liquid, and more specifically, refers to devices that are placed against or in proximity to the body of the wearer to absorb and contain the various exudates discharged from the body.

As used herein, the term "feminine hygiene article" refers to disposable absorbent articles to be worn by women for menstrual and/or light incontinence control. Feminine hygiene articles are typically held in place adjacent the user's externally-visible genitalia (i.e., the pudendal region) by the user's undergarment. Feminine hygiene articles can be placed into the user's undergarment and affixed via adhesive or other joining means. Feminine hygiene articles do not include baby diapers.

Figure 1:
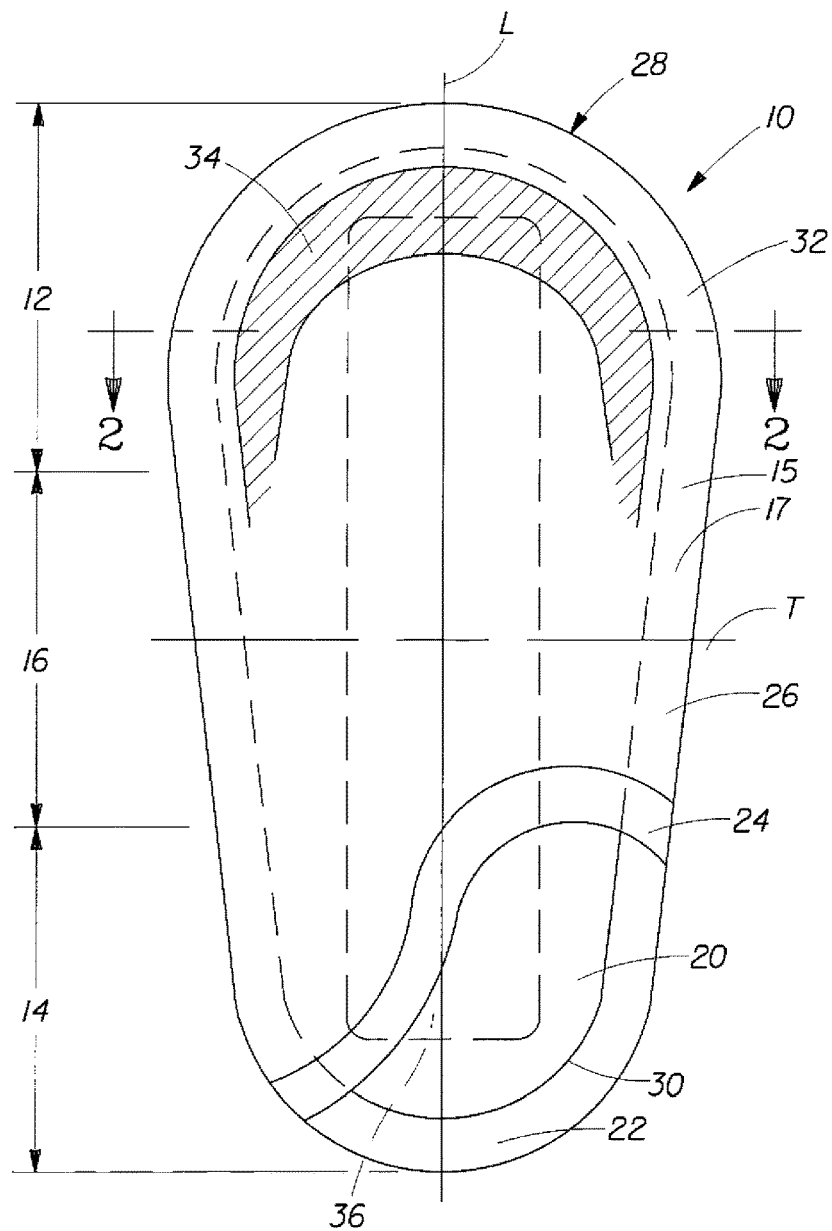
FIG. 1 is a partially cut away plan view of a feminine hygiene article of the present invention.
Figure 2:
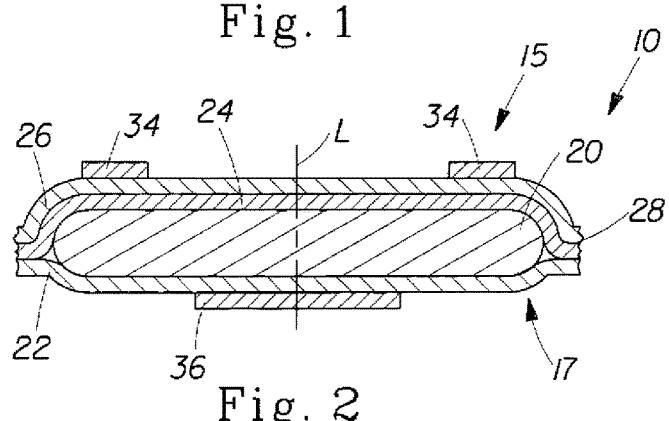
FIG. 2 is a cross-sectional view of the Section 2-2 as shown in FIG. 1.

One embodiment of a feminine hygiene article of the present invention, an incontinence pad 10, is shown in partially cut-away plan view in FIG. 1 and in cross section in FIG. 2. While the invention is disclosed in FIG. 1 as an embodiment of an incontinence pad 10, the disclosed features of the invention can also be useful when incorporated in other feminine hygiene articles, such as sanitary napkins and pantiliners. Therefore, the disclosure below is in the context of an incontinence pad, but is applicable to feminine hygiene articles in general. The invention can also be an anal discharge pad, a hemorrhoid pad, an interlabial pad, or any other absorbent article for which proper placement and orientation in an undergarment is desirable.

Incontinence pad 10 can be considered in three regions, two end regions 12 and 14 each comprising about one-third of the overall length, and a middle region 16. In the context of an incontinence pad 10 of the present invention, end region 12 represents the front of the pad, that is, the portion of the incontinence pad 10 intended to be oriented during use toward the front of the user's undergarment. In the context of a sanitary napkin or pantiliner 11 of the present invention, end region 12 represents the rear of the pad, that is, the portion of the sanitary napkin or pantiliner 11 intended to be oriented during use toward the rear of the user's undergarment.

Incontinence pad 10 has a body-facing surface (or side) 15 that is in contact with the user's body during use and a garment-facing surface (or side) 17 that is in contact with the user's undergarment during use. In general, each component layer of the incontinence pad 10 can be said to have a body-facing side and a garment-facing side, the sides being determined by their orientation relative to the in-use orientation of the article. Incontinence pad 10 has a longitudinal centerline L and a transverse centerline T, the centerlines being perpendicular to one another in the plane of the sanitary napkin when in a flat out configuration, as shown in FIG. 1. In one embodiment the incontinence pad can be generally symmetric about both centerlines, while in other embodiments the incontinence pad can be generally asymmetric about either centerline. In the embodiment shown in FIG. 1, incontinence pad 10 is symmetric about the longitudinal centerline L and asymmetric about transverse centerline T. As discussed more fully below, feminine hygiene articles can also be provided with lateral extensions known in the art as "flaps" or "wings" (not shown in FIG. 1) intended to fold over and cover the panty elastics in the crotch region of the user's undergarment.

Incontinence pad 10 can have any shape known in the art for feminine hygiene articles, including generally symmetric "hourglass" shaped, tapering inwardly from a relatively greater transverse width in a portion of one of the end regions to a relatively smaller transverse width at the middle region. However, the invention is particularly beneficial for incontinence pads and other feminine hygiene articles that are asymmetrical about the transverse axis, such that the maximum transverse width of one end, e.g., end region 12, of the pad is greater than the maximum transverse width of the other end, e.g., end region 14. Transverse width is defined herein as the edge-to-edge dimension across the article, measured parallel to the transverse centerline T. Such pads can be described as pear shaped, bicycle-seat shaped, trapezoidal shaped, wedge shaped, or otherwise described in a manner that connotes a two-dimensional shape having two ends in which one end is larger than the other in a maximum width dimension.

Incontinence pad 10 can have an absorbent core 20 to absorb and store bodily fluids discharged during use. In some embodiments of incontinence pads, pantiliners, sanitary napkins, or other such devices of the present invention, an absorbent core is not necessary, the pad consisting only of a topsheet (that can have some absorbency) and a fluid impermeable backsheet. Absorbent core 20 can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

In one embodiment absorbent core 20 can be relatively thin, less than about 5 mm in thickness, or less than about 3 mm, or less than about 1 mm in thickness. Thickness can be measured by any means known in the art for doing so while under a uniform pressure of 0.25 psi. The absorbent core can comprise absorbent gelling materials (AGM), including AGM fibers, as is known in the art.

Absorbent core 20 can be formed or cut to a shape, the outer edges of which define a core periphery 30. The shape of absorbent core 20 can be generally rectangular, circular, oval, elliptical, or the like. Absorbent core 20 can be generally centered with respect to the longitudinal centerline L and transverse centerline T.

To prevent absorbed bodily exudates from contacting the wearer's garments, incontinence pad 10 can have a liquid impermeable backsheet 22. Backsheet 22 can comprise any of the materials known in the art for backsheets, such as polymer films and film/nonwoven laminates. To provide a degree of softness and vapor permeability for the garment-facing side of sanitary napkin 10, backsheet 22 can be a vapor permeable outer layer on the garment-facing side of the sanitary napkin 20. The backsheet 22 can be formed from any vapor permeable material known in the art. Backsheet 22 can comprise a microporous film, an apertured formed film, or other polymer film that is vapor permeable, or rendered to be vapor permeable, as is known in the art. One suitable material is a soft, smooth, compliant, vapor pervious material, such as a nonwoven web that is hydrophobic or rendered hydrophobic to be substantially liquid impermeable. A nonwoven web provides for softness and conformability for comfort, and can be low noise producing so that movement does not cause unwanted sound.

To provide for softness next to the body, incontinence pad 10 can have a body-facing layer, referred to herein as topsheet 26. Topsheet 26 can be formed from any soft, smooth, compliant, porous material which is comfortable against human skin and through which fluids such as urine or vaginal discharges can pass. Topsheet 26 can comprise fibrous nonwoven webs and can comprise fibers as are known in the art, including bicomponent and/or shaped fibers. Topsheet 26 can also be a liquid permeable polymer film, such as an apertured film, or an apertured formed film as is known on sanitary napkins such as ALWAYS® brand sanitary napkins.

At least one, and preferably both, of topsheet 26 and backsheet 22 define a shape, the edge of which defines an outer periphery 28 of the incontinence pad 10. In a preferred embodiment, both topsheet 26 and backsheet 22 define the incontinence pad 10 outer periphery 28. The two layers can be die cut, as is known in the art, for example, after combining all the components into the structure of the incontinence pad 10 as described herein. However, the shape of either topsheet 26 or backsheet 22 can be independently defined.

Interposed between the absorbent core 20 and topsheet 26 can be at least one fluid permeable secondary topsheet 24. Secondary topsheet 24 can aid in rapid acquisition and/or distribution of fluid and is preferably in fluid communication with the absorbent core 20. In one embodiment, the secondary topsheet 24 does not completely cover the absorbent core 20, but it can extend laterally to core periphery 30. In one embodiment, topsheet, secondary topsheet, or the absorbent core can be layered structures, the layers facilitating fluid transport by differences in fluid transport properties, such as capillary pressure.

In one embodiment, absorbent core 20 does not extend laterally outward to the same extent as either topsheet 26 or backsheet 22, but the incontinence pad 10 outer periphery 28 can be substantially larger than the core outer periphery 30. In this manner, the region of incontinence pad 10 between the core periphery 30 and the incontinence pad 10 outer periphery 28 can define a breathable zone 32 that permits vapors to go through portions of the sanitary napkin, thereby escaping and providing for dryer comfort when worn. The breathable zone incontinence pad having a breathable zone can be according to the teachings of U.S. Ser. No. 10/790, 418, filed Mar. 1, 2004.

All the components can be adhered together with adhesives, including hot melt adhesives, as is known in the art. The adhesive can be Findlay H2128 UN or Savare PM 17 and can be applied using a Dynafiber HTW system.

As is typical for sanitary napkins and the like, the incontinence pad 10 of the present invention can have panty fastening adhesive 36 disposed on the garment-facing side 17 of backsheet 22. Panty fastening adhesive 36 can be any of known adhesives used in the art for this purpose, and can be covered prior to use by a release paper, as is well known in the art.

The above disclosure is meant to give a general description of the basic parts of feminine hygiene articles such as sanitary napkins and incontinence pads and the like as they are known in the art. The description is not intended to be limiting. Any and all of various known elements, features and processes of known sanitary napkins, pantiliners, incontinence pads, and the like can be incorporated in the feminine hygiene article of the present invention as desired or needed for particular use benefits. For example, sanitary napkins can be according to the disclosure of U.S. Pat. No. 4,950,264 issued to Osborn III Aug. 21, 1990, and an incontinence pad can be according to the disclosure of U.S. Pat. No. 5,439,458 issued to Noel et al. Aug. 8, 1995. Now, with respect to the remaining disclosure, the novel features and benefits of the present invention will be described.

Feminine hygiene articles of the present invention can be symmetric about both the longitudinal and transverse centerlines. However, the invention is most useful in the context of feminine hygiene articles that are characterized by asymmetry, either in shape or in functional parameters. For example, in one embodiment, a feminine hygiene article is symmetrically-shaped about both the longitudinal and transverse centerlines, but is functionally asymmetric in that it is functionally enhanced in one region offset with respect to at least one centerline, for example, by having more absorbent capacity disposed nearer a first end region relative to a second end region. In such a pad, it is important that the user perceive which end of the pad is functionally enhanced to facilitate proper choice of article for an intended use as well as for proper placement in the undergarment. In one embodiment, a feminine hygiene article is asymmetric about the transverse centerline, such that one end is functionally enhanced by having a greater surface area. Again, it is important that the user perceive the larger surface area portion as being functionally-enhanced for the particular use of the pad. That is, aside from the perimeter shape of the article and the difference in surface area between one end and the other, the user can benefit from a visual or tactile indicator to aid in proper, i.e., front or rear, orientation of the larger surface area.

Therefore, as disclosed fully below, a feminine hygiene article of the present invention comprises a functional enhancement indicator 34 to aid the user in proper choice of article and proper placement and use of the article. Functional enhancement indicator 34 can be an indication or a signal perceptible to the user that corresponds to a functionally-distinguishable portion of a feminine hygiene article. A functionally-distinguishable portion of a feminine hygiene article is a portion that is different in composition, configuration, or construction from relative to adjacent portions of the article. Functional enhancement indicator 34 can be an indication or a signal perceptible to the user that corresponds to a functionally-distinguishable portion of a feminine hygiene article that is otherwise not perceptible to the user. Functional enhancement indicator 34 can be an indication or a signal perceptible to the user that corresponds to a functionally-distinguishable portion of a feminine hygiene article that is otherwise not perceptible to the user as being intended for the particular function indicated. In one embodiment, functional enhancement indicator 34 applied by printing, such as by ink-jet printing. In one embodiment functional enhancement indicator 34 applied only by printing, such as by ink-jet printing, onto one of the article components, and does not include a previously colored, or dyed component, such as a uniformly-colored non-woven.

Functional enhancement indicator 34 can be only visually perceptible, i.e., a visually-perceptible functional enhancement indicator. Functional enhancement indicator can be only tactilely perceptible, i.e., a tactilely-perceptible functional enhancement indicator. Functional enhancement indicators are disclosed below primarily in a preferred embodiment of being visually perceptible. By "visually perceptible" is meant that a human viewer can visually discern the functional enhancement indicator with the unaided eye (excepting standard corrective lenses adapted to compensate for near-sightedness, farsightedness, or stigmatism, or other corrected vision) in lighting at least equal to the illumination of a standard 100 watt incandescent white light bulb at a distance of 1 meter. By "only visually perceptible" is meant that the functional enhancement indicator cannot be readily perceived on the body-facing surface of the feminine hygiene article by touch, sound, or smell. Therefore, channels, embossments, tufts, folds, pleats, and other tactilely-perceptible elements of a feminine hygiene article are not considered to be only visually perceptible. However, a functional enhancement indicator that is only visually perceptible can be used in conjunction with such channels, embossments, and the like. For example, a functional enhancement indicator can be used in conjunction with edge crimping about the periphery of an incontinence pad to signal enhanced fluid containment.

Functional enhancement indicator 34 can be disposed off-center of the feminine hygiene article; that is, it can be a visually-perceptible mark or signal that is itself not centered with respect to at least the transverse centerline T. In one embodiment, as shown in FIG. 1, functional enhancement indicator 34 is off center with respect to the transverse centerline, but is symmetric with respect to the longitudinal centerline. In this manner, functional enhancement indicator 34 can identify one end region of a feminine hygiene article as being a region of particular functional significance, for example, as the region of intended fluid entry. Functional enhancement indicator 34 can also signal the front of an incontinence pad 10 to indicate to the user the portion of the article intended to be placed for the function of absorbing urine and vaginal discharge. Functional enhancement indicator 34 can also identify a region of the pad having other enhanced functionality, such as greater absorbency, greater fluid containment, less leakage, better dryness, better sensate concentration, greater odor control additives, or the like.

As shown in FIG. 1, incontinence pad 10 can be asymmetric about the transverse centerline T. One way of describing such an incontinence pad 10 is to say that one of the end regions 12 or 14 has a greater surface area on a body-facing surface thereof than the other. Such an article, when properly placed in an undergarment can result in more coverage, e.g., more of the surface area of the pad, toward either the front or the rear of the user's undergarment during use. For sanitary napkins, consumers typically place the larger end region 12 toward the rear of the panty for better protection from soiling. However, an asymmetric design for incontinence pads presents a problem to the user. Because the pad is not designed for the larger end portion 12 to be oriented to the rear of the undergarment, the user benefits from a visual signal to reinforce the intended orientation of the pad. The visual signal is believed to be necessary to overcome the user's force of habit since users typically place asymmetric feminine hygiene articles such that the larger end portion is oriented to the rear portion of the user's undergarments.

To solve the above problem, a feminine hygiene article, e.g., incontinence pad 10 of the present invention, has at least one functional enhancement indicator 34 visible from the body-facing surface 15 of incontinence pad 10 and providing a distinct visual emphasis to a portion of the pad nearer to one of the first or second end regions 12 or 14. In the context of an incontinence pad 10, for example, the functional enhancement indicator 34 can be a mark or signal that provides a visually-perceptible indication of the front of the pad to facilitate proper orientation of the incontinence pad 10 with respect to the undergarment when placing and positioning the incontinence pad 10 in an undergarment, such as the panty of the wearer.

Functional enhancement indicators 34 can comprise printed indicia, such as ink-jet-printed figures, designs, lines or line segments, or embossed ridges or bumps, folds, pleats, or any other means known in the art for providing visible indications that serve the function of distinguishing one portion of a feminine hygiene article from the other, for example to aid the user in determining proper front to back orientation placement of an asymmetrically-shaped incontinence pad in an undergarment. Specifically, as shown in FIG. 1, functional enhancement indicators 34 can be disposed so as to indicate which end region of the incontinence pad 10 is intended to be, or to bound, the region of fluid entry. Thus, for an incontinence pad 10, functional enhancement indicator 34 provides a visually-perceptible distinctiveness that indicates to the user that the larger end portion 12 of pad 10 is intended to be oriented to the front of the user's undergarment.

Therefore, one criteria for functional enhancement indicator 34 is that it clearly identify one portion, such as one end portion, of the article as being functionally different from other portions by a visual signal distinct from the overall shape of the article about its periphery, which shape may, in fact, provide the user with an opposite intuitive response. One way of describing an asymmetric article of the present invention, therefore, is the article has two end portions each differing from the other in maximum width measured parallel to a transverse centerline, and differing in surface area measured with respect to the periphery and the transverse centerline, but which article comprises a visually-perceptible signal to the wearer, the visually-perceptible signal distinctly identifying one end portion of the article as being a region of particular significance, for example, as the region of intended fluid entry. The perception of the user may be that the indicated portion of the pad may be one of greater absorbency, greater fluid containment capacity, less leakage, better dryness, better odor control, improved softness, or other signals that facilitate an intuitive response to orient the functional enhancement indicator properly, e.g., to the front of the undergarment.

For asymmetrically-shaped incontinence pads, the effect of functional enhancement indicator 34 is to give the user of an incontinence pad 10 a visual signal as to the portion of the pad intended to be oriented to the front of the wearer's panties when worn for incontinence control. Because the user's intuitive notion is to place the pad "backwards" having the larger portion oriented to the rear of her panties, the visual signals presented by the functional enhancement indicator 34 of the present invention provides the benefit of improved use through correct orientation in the undergarment. The user's attention is drawn to the distinctive region signaled by the functional enhancement indicator 34, triggering a response that such a region is functionally important for its intended use. Therefore, for incontinence pads with an intended use of absorbing urine, the user instinctively orients the pad with the larger surface area portion toward the front of her undergarment during use.

Functional enhancement indicators 34 can be disposed on or in the feminine hygiene article so as to be visible from the body-facing surface 15 such that an indication is made to the user calling attention to the significance of the indicated portion of the article. Functional enhancement indicators can indicate a region of enhanced functionality, such as a region of enhanced absorbency, enhanced fluid capacity, enhanced leakage control, enhanced odor control, enhanced surface treatment of lotions or skin care agents, and the like. Functional enhancement indicators can signal a region of enhanced fluid containment, and can comprise additional fluid containment features, such as channels, gel-blocking coatings, and the like as is known in the art. Functional enhancement indicators 34 can also be used in conjunction with fit guides for use in the proper positioning in the undergarment, such as fit guides disclosed in U.S. Ser. No. 10/852,709, filed by Digiacomantonio et al.

Figure 3:
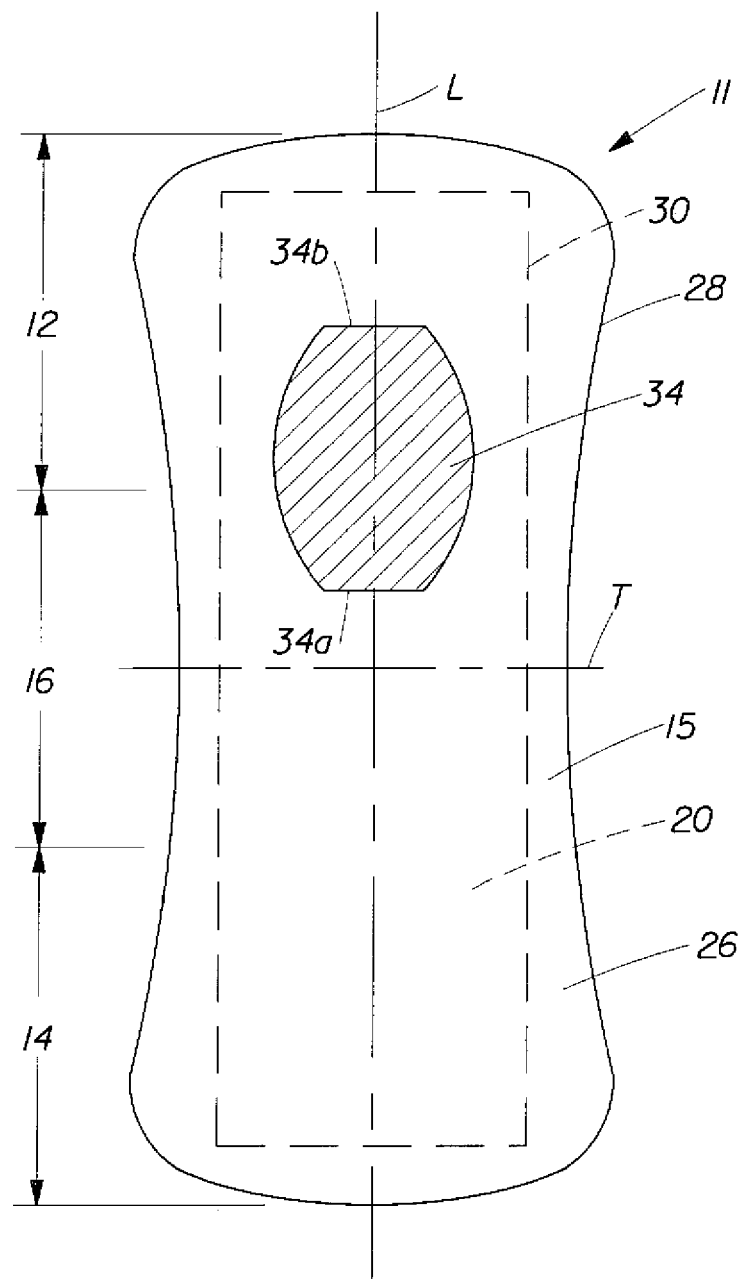
FIG. 3 is a plan view of a feminine hygiene article of the present invention.

FIG. 3 shows a feminine hygiene article which is a sanitary napkin 11 that is symmetrically-shaped about both a longitudinal centerline L and a transverse centerline T. A functional enhancement indicator 34 is disposed generally symmetrically about longitudinal axis L, and off center, placed nearer first end region 12 with respect to transverse centerline T. Functional enhancement indicator 34 as shown in FIG. 3 is fully on one side of transverse centerline T. In other embodiments, the functional enhancement indicator can extend on both sides of transverse centerline T. In such a case, functional indicator is considered nearer first end 12 if one of a first edge 34A or a second edge 34B of the functional enhancement indicator 34 is closer to an end edge of the feminine hygiene article than the other.

The functional enhancement indicator 34 can be printed on the topsheet 26 or on the underlying absorbent core 20 or on another portion of sanitary napkin 11 as long as it is visually perceptible from the body-facing surface 15 thereof. The region of sanitary napkin 11 corresponding to the portion of the sanitary napkin 11 marked by functional enhancement indicator 34 can be a region of enhanced absorbency. For example, the absorbent core 20 can have a higher basis weight, or a greater concentration of absorbent gelling material (AGM), or a greater thickness, or other means of greater absorbency in the region of the sanitary napkin 11 indicated by functional enhancement indicator 34. Thus, functional enhancement indicator 34 can aid the user orienting and placing the sanitary napkin in her undergarment so as to make the best use of the enhanced absorbency.

Functional enhancement indicators 34 can be printed on a surface visible from the body-facing surface of sanitary napkin 10. Functional enhancement indicators 34 can be printed on a surface below the topsheet 26 as long as it is visible to the user during placement and positioning of the article in the undergarment. Therefore, functional enhancement indicators 34 can be ink or dye printed, coated, sprayed, or otherwise disposed on, secondary topsheets, surge layers, acquisition layers, absorbent cores, and the like. Functional enhancement indicators 34 can be configured as lines, line segments, curved lines, bands, arrows, words, pictures, or any other printed indicia having a purpose of providing a signal or guide to the user for proper use with respect to the functional enhancement of the article. Again, the visual indicia need not be printed on the body-facing side 15 of a feminine hygiene article, but need only be visible from the body-facing side thereof such that the user can see the indicia as she places the article in, or removes the article from, her undergarment.

Figure 4:
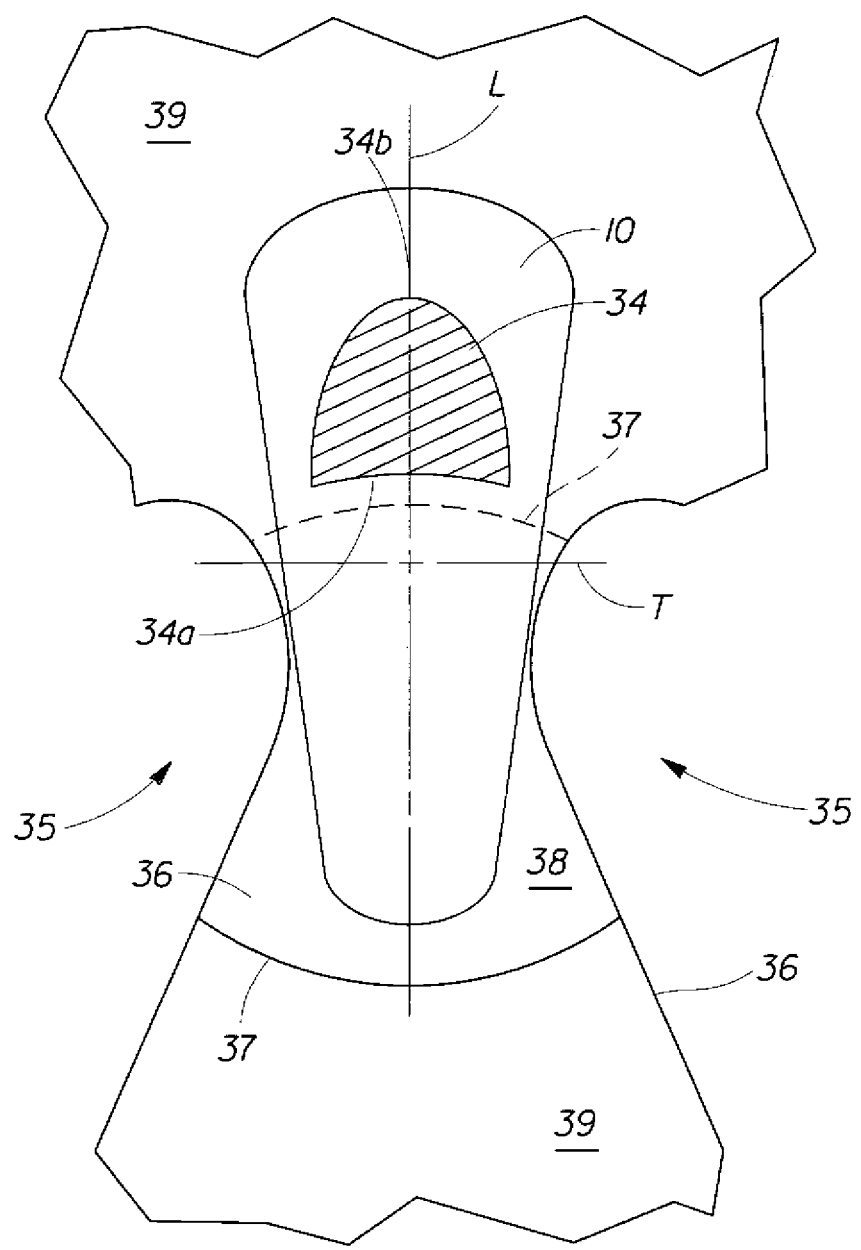
FIG. 4 is a plan view of a feminine hygiene article of the present invention properly positioned in an undergarment.

FIG. 4 shows an incontinence pad 10 properly positioned in the crotch portion 38 of a panty 39. Incontinence pad 10 shown in FIG. 4 is an example of an article of the present invention not having flaps intended to wrap the edges of the leg openings of the undergarment. As shown in FIG. 4, portions of the panty 39 defining leg openings 35, such as leg elastics 36, can be positioned to coincide tangentially with side edges of incontinence pad 10 when the incontinence pad 10 is properly placed in the crotch region 38 of the panty. Therefore, proper placement and orientation of incontinence pad 10 can be achieved by utilizing functional enhancement indicator 34 to indicate the portion of the incontinence pad 10 intended to be oriented to the front of the panty, and by utilizing side edges to indicate proper front-to-back positioning, if desired. Further, to aid in placing and positioning the incontinence pad 10 properly, in one embodiment functional enhancement indicators 34 can be disposed so as to indicate proper alignment of the feminine hygiene article 10 with respect to the curvature of leg openings 35 of the undergarment 39.

Functional enhancement indicators 34 can be placed so as to give the user a visual indication of proper placement of the article in the undergarment by providing a visual indication on the portion of the article that is to be oriented to the front of the wearer, which, in FIG. 4 is oriented toward the top of the page. As shown in FIG. 4, functional enhancement indicator 34 can have shapes and visual definition and distinctiveness to provide other clues as to proper orientation and placement. For example, first edge 34A of functional enhancement indicator 34 can be associated with the rearward or "back" portion of the functional enhancement indicator 34, and a second edge 34B can be associated with forward or "front" portion of the functional enhancement indicator 34. In the embodiment shown in FIG. 4, first edge 34A has a curvature that is generally similar to that of a seam 37 of the undergarment, such as a seam of a sewn-in crotch panel. In addition, the generally pointed shape of second edge 34B can indicate a direction of orientation to the user to indicate the front of the pad with respect to the wearer's body and undergarment.

Figure 5:
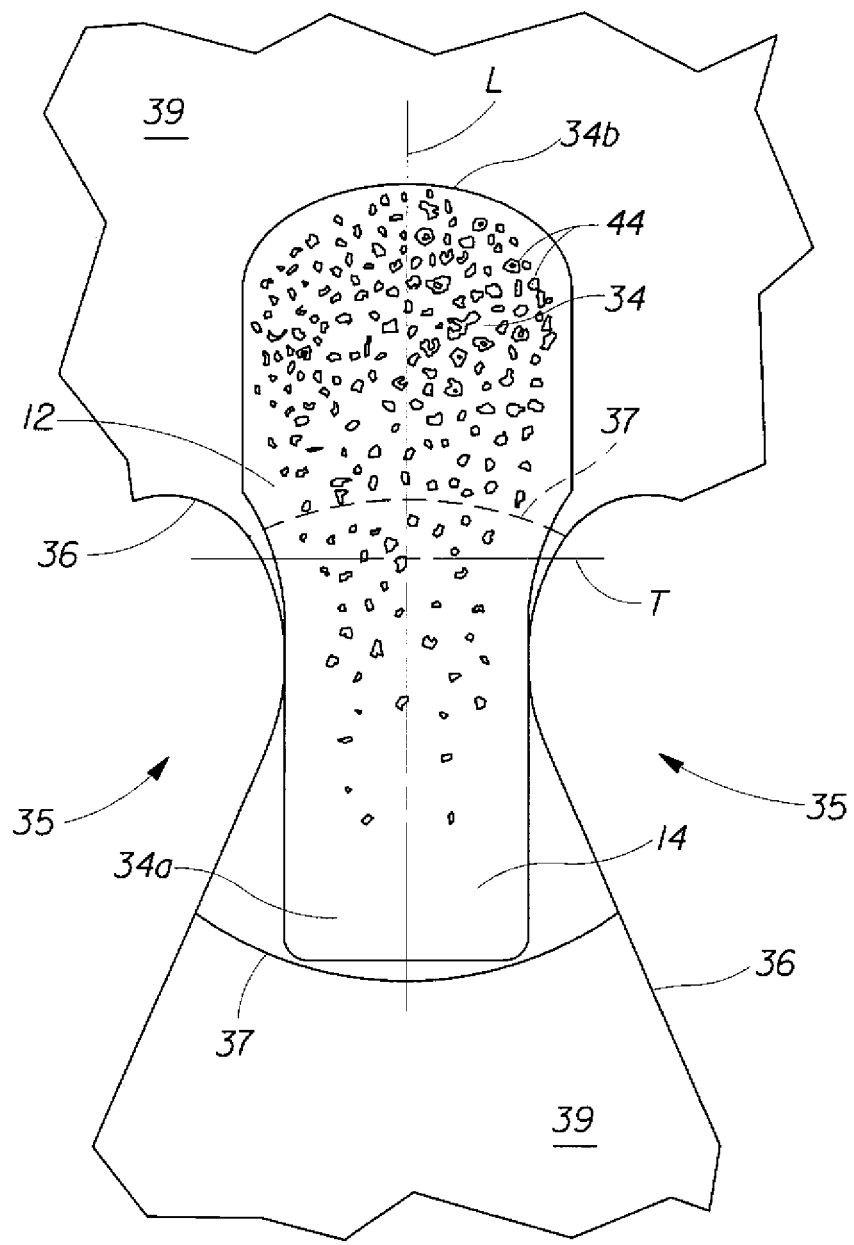
FIG. 5 is a plan view of another embodiment of a feminine hygiene article of the present invention properly positioned in an undergarment.

In one embodiment, as shown in FIG. 5, functional enhancement indicator 34 can be a visual signal characterized by a gradient in visual emphasis. The gradient in visual emphasis can be the result of a gradient of color intensity, for example, or a gradient in density of visually-perceptible discrete elements. For example, functional enhancement indicator 34 can be a pattern of visually-perceptible dots or speckles 44 placed in a pattern of increasing density from the first edge 34A to the second edge 34B. In such an embodiment, the term "edge" is used to indicate the front and rear boundaries of functional enhancement indicator 34 parallel with the transverse centerline T. In general, first and second edges 34A and 34B bound every portion of functional enhancement indicator 34 from front to back along longitudinal centerline L. In some embodiments first and second edges 34A and 34B of can be coincident with portions of the perimeter 28 of the incontinence pad 10.

As shown in FIG. 5, discrete visual elements such as dots or speckles can be distributed on a portion of incontinence pad 10, such as on topsheet 26 or secondary topsheet 24, to be visible as a uniform gradient of increasing density. Thus, even though first and second edges 34A and 34B of can be nearly equidistant to their respective end edges of the article, the functional enhancement indicator 34 can be readily seen as being weighted in visual emphasis toward first end region 12 as opposed to second end region 14. In another embodiment, the gradient can be non-uniform, and can be localized predominantly in the end region 12 of the pad to further emphasize the portion of the pad to be oriented to the front of the wearer's undergarment 39.

Functional enhancement indicator(s) 34 can be made by printing, stamping, embossing, folding or any other known process that makes a visual, or even tactile, impression that indicates a portion of the feminine hygiene article as being enhanced for a particular use. Functional enhancement indicator 34 can be a shaded, striped, stippled, or other noncontiguous region. Functional enhancement indicator 34 can be shaded such that the visual impression is one of a continuous colored band. In one embodiment the continuous colored band can be of one or more colors that increase in intensity from one portion of the incontinence pad 10 to another. By "increase in intensity" is meant an increase in the intensity of the hue, saturation, color, or a combination of color characteristics. In one embodiment functional enhancement indicator 34 can comprise one color; in another embodiment functional enhancement indicator 34 can comprise more than one color. Printing can be by known processes, such as gravure printing, offset printing, inkjet printing, and combinations thereof. In one embodiment functional enhancement indicator 34 can be made by ink jet printing a predetermined pattern on a portion of an incontinence pad 10 such that the pattern is visible to the user when viewing the body-facing side 15 of incontinence pad 10. In one embodiment, ink can be printed directly on the topsheet. In another embodiment color can be printed on a portion of the incontinence pad below the topsheet, but visible through the topsheet.

Figure 6:
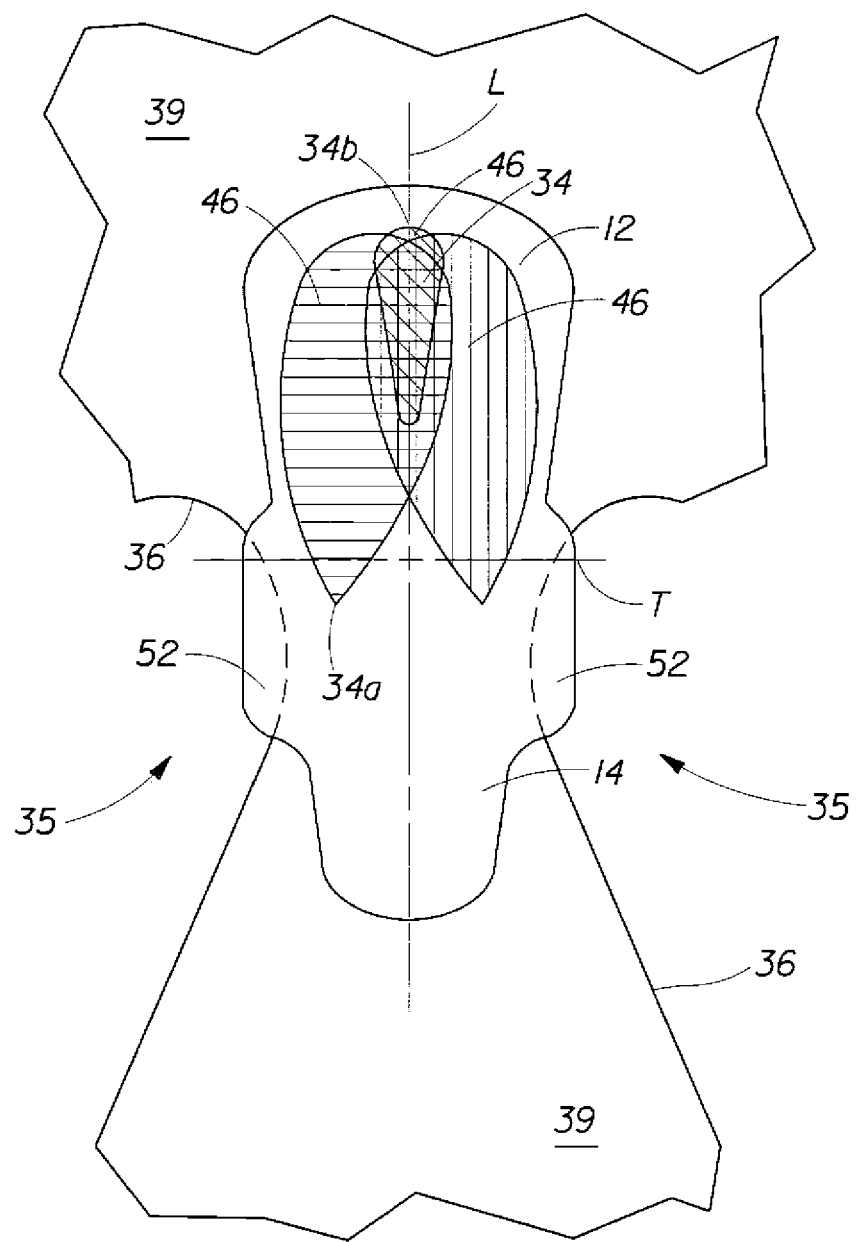
FIG. 6 is a plan view of another embodiment of a feminine hygiene article of the present invention properly positioned in an undergarment.

FIG. 6 shows an incontinence pad 10 having flaps 52 that are intended to fold over and wrap the leg elastics of the undergarment (flaps 52 in FIG. 6 are shown in an unfolded, flat condition). Flaps 52 can have attachment means (not shown) to affix the sanitary napkin to the underside of the undergarment, as is known in the art. Any of various attachment means known in the art can be used with the present invention, including pressure sensitive adhesive means, in which case release strips can be incorporated as well. It is known to make a line of weakness or a flexible zone to facilitate folding of flaps on sanitary napkins.

As shown in FIG. 6, functional enhancement indicator 34 can comprise a single colored region or a plurality of colored regions. A plurality of colored regions can be disposed as overlapping regions 46 of color to define a color gradation or change in intensity by virtue of the overlapping nature of the regions. As shown, for example, a plurality of colored or shaded regions 46 (three are shown in FIG. 6) can be individually printed or otherwise applied in a manner to define a darker or more intense region in the areas of region overlap. Colored or shaded regions 46 can be any shape, including shapes evoking pleasant feelings, such as flower petals, sun rays, ocean waves, and the like. The colors of colored or shaded regions 46 can be uniform, or they can be varying shades or hues of one color, or they can be different colors. The functional enhancement indicator 34 can be a feature of a feminine hygiene article together with other printed indicia or features, such as the above-mentioned fit guides.

Figure 7:
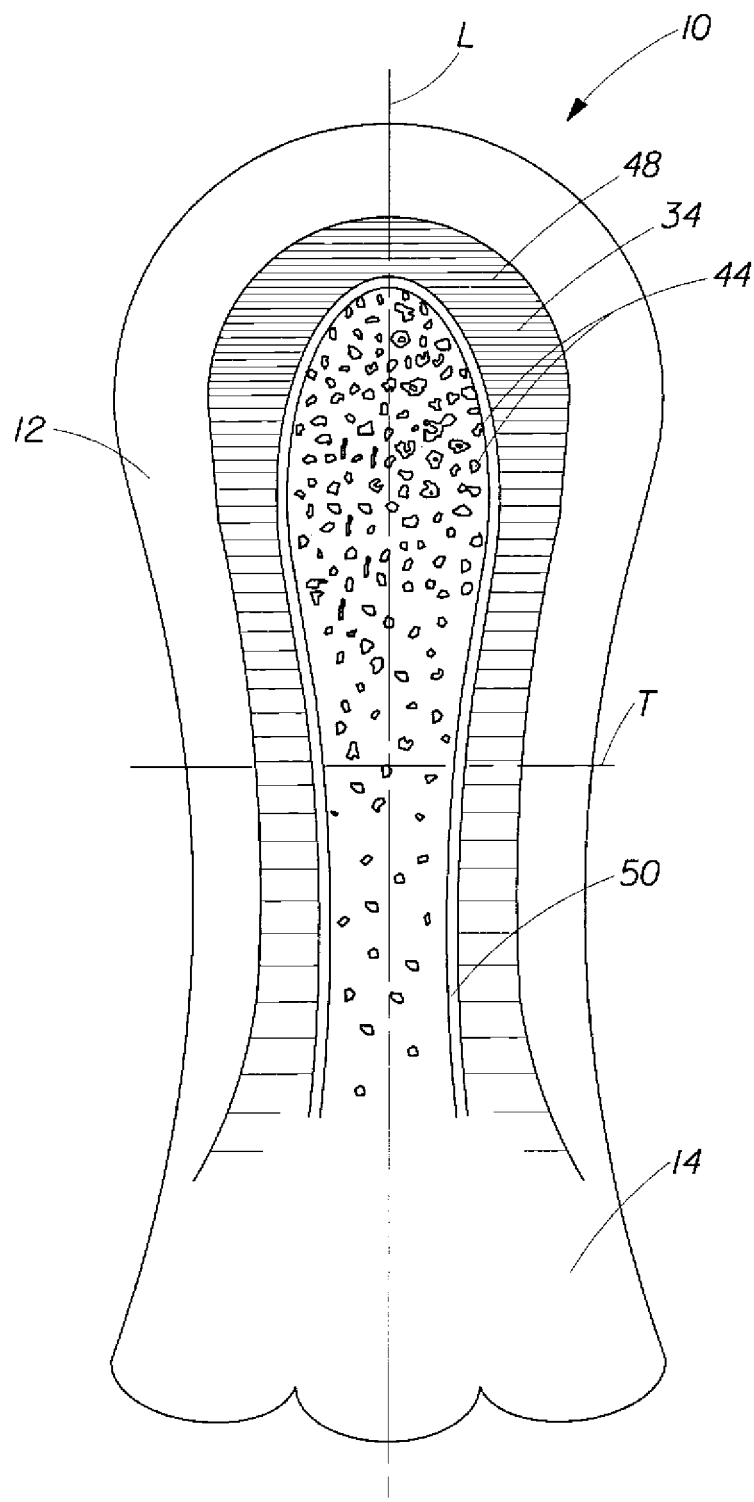
FIG. 7 is a plan view of another embodiment of a feminine hygiene article of the present invention.

Another embodiment of incontinence pad 10 is shown in FIG. 7. As shown in FIG. 7, functional enhancement indicator 34 can comprise a plurality of different visual effects, all of which draw a visually-perceptible distinction to a predetermined portion or portions of a feminine hygiene article. For example, functional enhancement indicator 34 can comprise a region of dots or speckles 44 in an array of increasing density from one region of incontinence pad 10 to another. In addition, to reinforce the visual indication of the front-oriented portion of incontinence pad 10, a band of color 48 of changing color intensity can be applied, the greater color intensity indicating the front-oriented portion of incontinence pad 10. Further, in addition to, or individually, an embossed channel 50 can be disposed on the body-facing surface of incontinence pad 10 to give a visual indication of the desired location of fluid entry and containment. Embossed channel 50 can be a continuous depression, or a series of individually-compressed, closely-spaced embossments. Embossing can be achieved by means well known in the art. In one embodiment, functional enhancement indicator 34 is only visibly perceptible, that is, it includes only the visually perceptible portion of the article, and not the tactilely perceptible portion, such as the channel. That is, in one embodiment, functional enhancement indicator 34 excludes embossments, channels, and the like.

Figure 8:
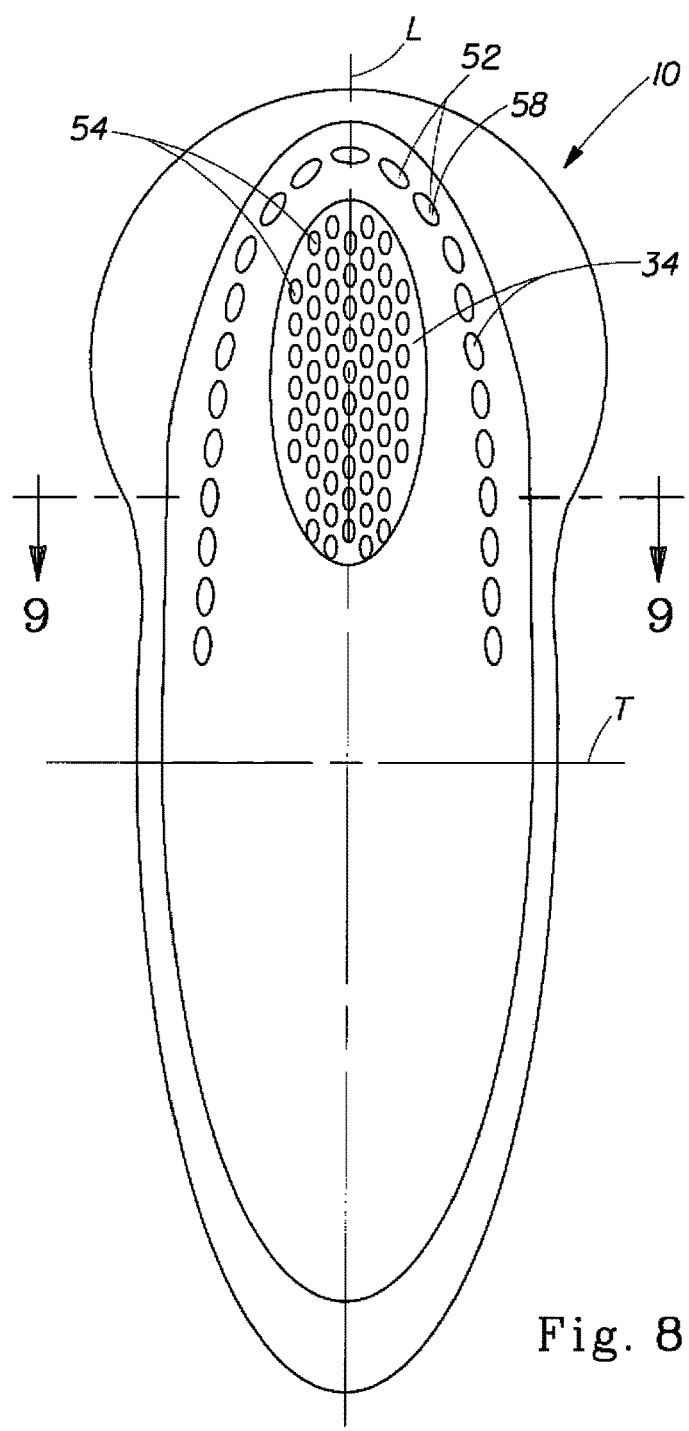
FIG. 8 is a plan view of another embodiment of a feminine hygiene article of the present invention.
Figure 9:
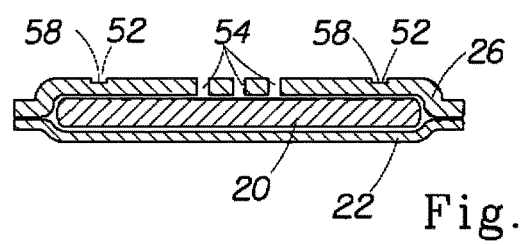
FIG. 9 is a cross-sectional view of the section 9-9 as shown in FIG. 8.

FIG. 8 illustrates another embodiment of the present invention combining embossing and printing or other methods known in the art for imparting color, as well as apertures to make functional enhancement indicators 34. As shown in FIG. 8, incontinence pad 10 can comprise functional enhancement indicator 34 comprising a plurality of embossments 52 that together form a curvilinear visually-distinct functional enhancement indicator 34. As shown in the cross section of FIG. 9, one or more of the embossed depressions 52, or all the embossed depressions, can have therein a substance such as ink to provide visible color 58. The visible color can be printed in registration with the embossments, or printed at the same time as the embossments are made by means known in the art, such as the method described in WO 04/057110, or U.S. Pat. No. 6,780,270. The color 58 can be due to printing inks, dyes, paint, or colored adhesive. The color 58 can also be under the topsheet, even on a separate layer (neither shown in FIG. 8), such that upon embossing, color 58 shows through the embossed portion, thereby giving the appearance of having been printed in registration with the embossed functional enhancement indicator 34.

Also shown in FIG. 8, functional enhancement indicator 34 can comprise a plurality of visually perceptible apertures grouped in a distinct manner so as to give a visual indication of a region of enhanced absorbency, or otherwise indicating the region of enhanced functionality. Apertures can be visually perceptible and yet not tactilely perceptible. Apertures 54 can be formed by means known in the art, including the method described in U.S. Pat. No. 5,628,097 and WO 01/45616.

In another embodiment, a functional enhancement indicator 34 can be achieved by having functional enhancement indicator components that are only tactilely sensed, i.e., not visibly sensed. Such a tactile feature can serve as a functional enhancement indicator 34 by means of a change in surface smoothness, a change in the coefficient of friction, or other tactilely-sensed change in material properties. In general, the change in material properties can correspond in location to the visible functional enhancement indicators 34 as disclosed herein.

Figure 10:
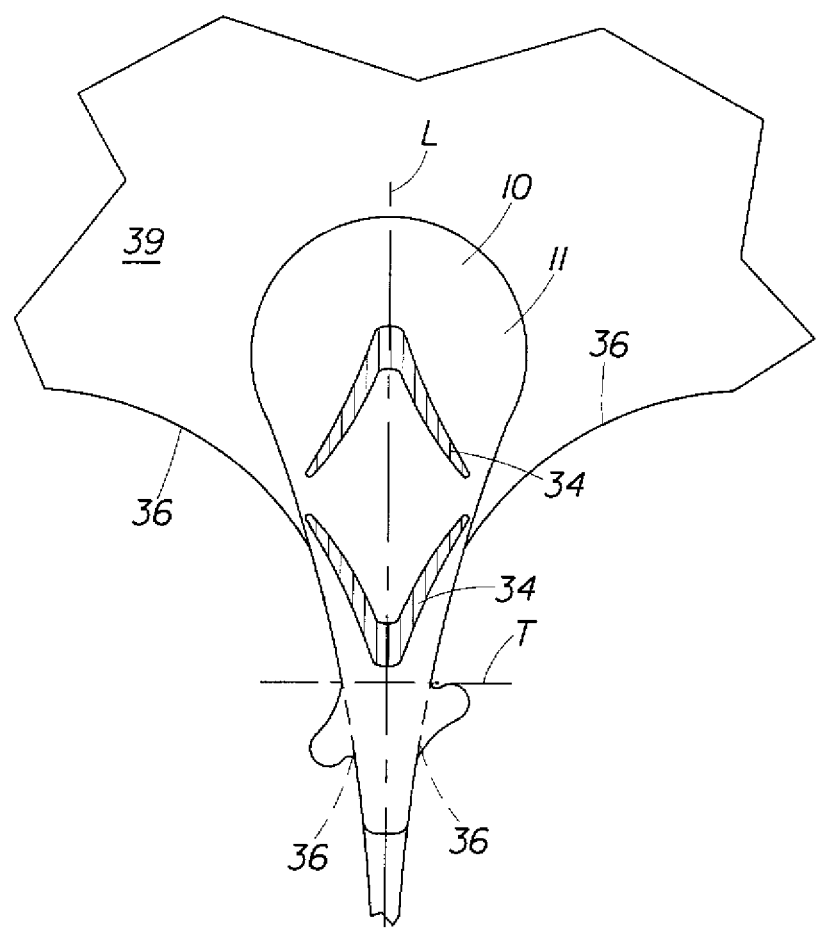
FIG. 10 is a plan view of another embodiment of a feminine hygiene article of the present invention.

An example of an incontinence pad 10 that is neither symmetric about the longitudinal axis L nor the transverse axis T is shown in FIG. 10. FIG. 10 shows an incontinence pad 10 or pantiliner 11 designed for use in a so-called thong, or string panty. The very narrow crotch width can require flaps 51, if used, to be offset with respect to one another so as to avoid overlapping. As shown, a functional enhancement indicator 34, in this case a pair of printed, colored, stylized "V" shapes, can indicate a region of fluid entry or a region of enhanced absorbency or a region of enhanced fluid containment.

Figure 11:
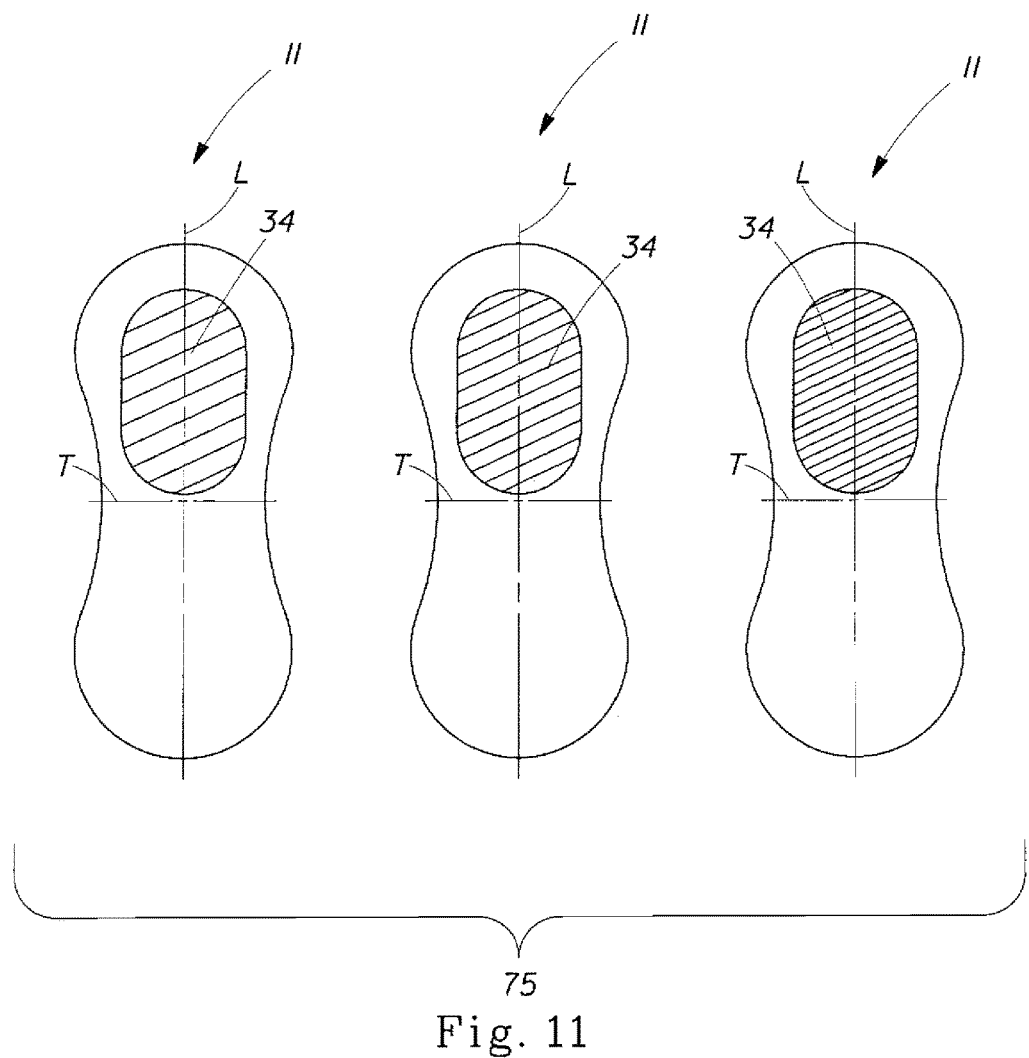
FIG. 11 is a view of an array of feminine hygiene articles of the present invention.

Feminine hygiene articles designed for use in so-called thong, or string panties, as shown in FIG. 10 can be described as having one end that tapers to a very narrow width. For example, a sanitary napkin designed for use in a string panty can taper at one end to an edge-to-edge width of about 27 mm (measured 10 mm from the narrowest end of the article and parallel to a transverse centerline). In one aspect of the present invention, such highly-asymmetrically-shaped articles can be most benefited by use of a functional enhancement indicator since slight misplacement to the front or rear with respect to the panties can make a large difference in performance. Therefore, in one embodiment of the present invention, feminine hygiene articles include those that can be described as having a minimum edge-to-edge width measured about 10 mm from one end and parallel to the transverse centerline of less than about 30 mm Other embodiments, which can be termed "non-thong feminine hygiene articles," can be characterized as having a minimum edge-to-edge width measured parallel to the transverse centerline of greater than about 30 mm. In another embodiment, feminine hygiene articles of the present invention can be characterized as having a minimum edge-to-edge width measured at and parallel to the transverse centerline of greater than about 30 mm In another embodiment, feminine hygiene articles of the present invention can be characterized as having an absorbent core member having a minimum edge-to-edge width measured parallel to the transverse centerline of greater than about 30 mm Functional enhancement indicator(s) 34 can be beneficially utilized to distinguish between pads in an array of feminine hygiene articles that are otherwise substantially identical in appearance. FIG. 11 shows an array 75 of three sanitary napkins 11 by way of example, in which each of the three sanitary napkins 11 differ with respect to a functional characteristic. For example, each sanitary napkin 11 in FIG. 11 can differ in absorbent capacity, odor control, sensate delivery, lotion delivery, skin care agent concentration, or any other functional attribute beneficial in the context of a feminine hygiene article. As depicted in FIG. 11, the functional enhancement indicator 34 increases in visual emphasis in the array 75 from the first pad on the left to the last pad on the right. The increase in visual emphasis can be due to an increase in color intensity or color density from pad to pad, or line density, or any other visual indicia that gives the user a visually-distinct signal as to the relative amount of the relevant functional enhancement. In one embodiment, a plurality of sanitary napkins can be sold in the same package as an array 75 of feminine hygiene articles, with the functional enhancement indicator 34 on each aiding the user in choosing a particular sanitary napkin for a given personal circumstance. For example, functional enhancement indicators 34 in FIG. 11 can indicate relative amounts of absorbent capacity, and the user can use the visual indication to choose a pad for her particular flow at a particular time.

Figure 12:
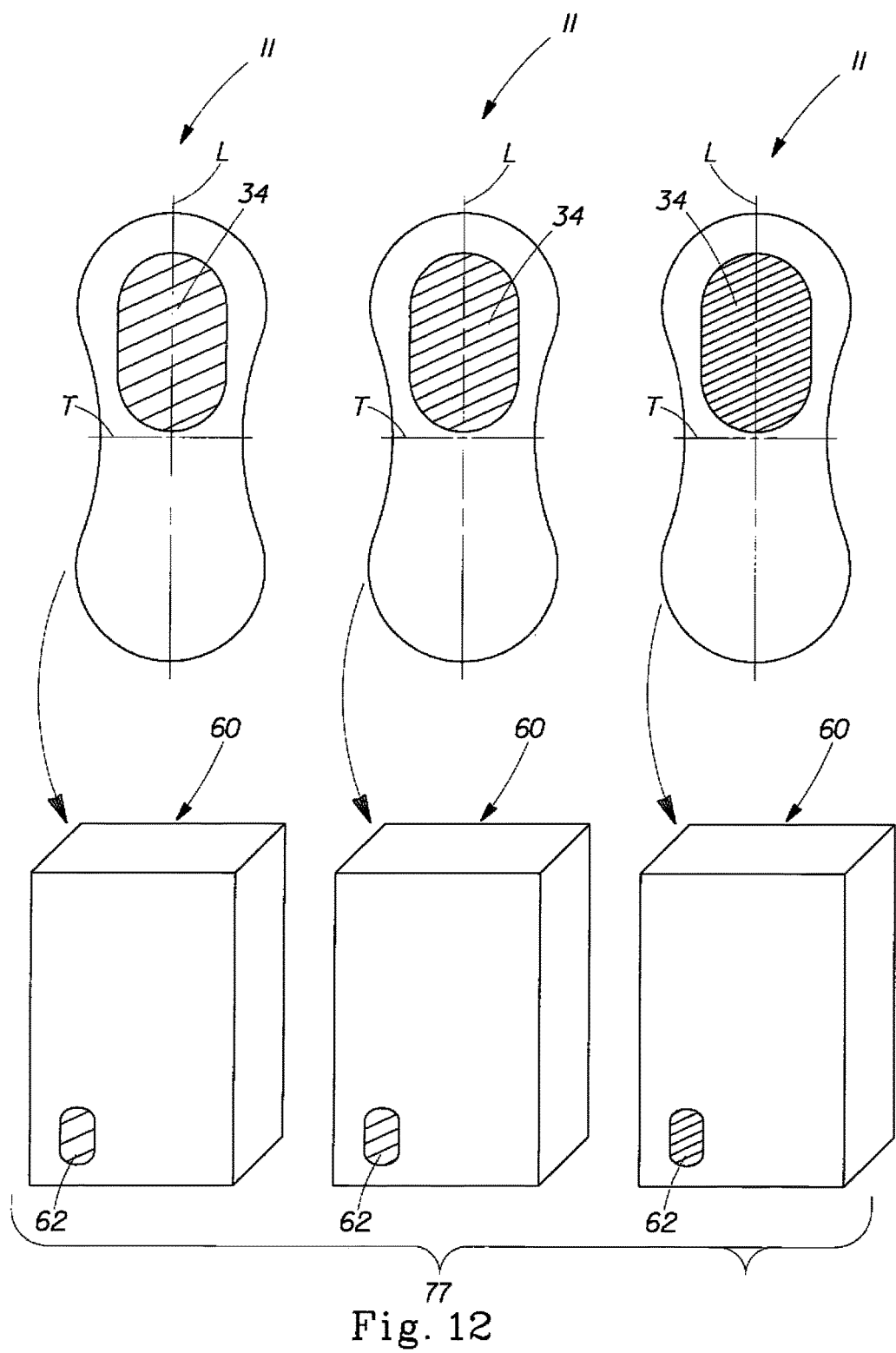
FIG. 12 is a view of an array of feminine hygiene articles and a corresponding array of packaging of the present invention.

In another embodiment, feminine hygiene articles of a given functional characteristic can be packaged in containers such as bags, boxes, or cartons, which carry a similar visual signal to aid a user in choosing an appropriate pad for an appropriate function. For example, as shown in FIG. 12, the sanitary napkins described in FIG. 11 can be packaged in an array 77 of boxes or cartons 60 bearing a visual signal or indicator 62 that corresponds in visual distinction to functional enhancement indicator 34. Thus, if functional enhancement indicator 34 is a shade of color, visual indicator 62 can be a matching or substantially-matching shade of color. By "substantially-matching" is meant the color is close enough that the pad and the packaging can be easily matched by one comparing pads and packaging. For example, substantially-matching shades can be matching within the range of normal variance of colors from lot to lot of ink, dye, or other color-inducing medium, or within normal variance due to slight differences perceived on film versus paper, and the like. Other means of obtaining corresponding visual distinction include matching the shapes, styles, or overall appearance of visual indicators 62 with corresponding functional enhancement indicators 34. A consumer or user of feminine hygiene articles can choose a feminine hygiene article having a desired functional characteristic more easily based on the packaging, with a confirmation or reinforcement of that functional characteristic on each pad inside the packaging.

Figure 13:
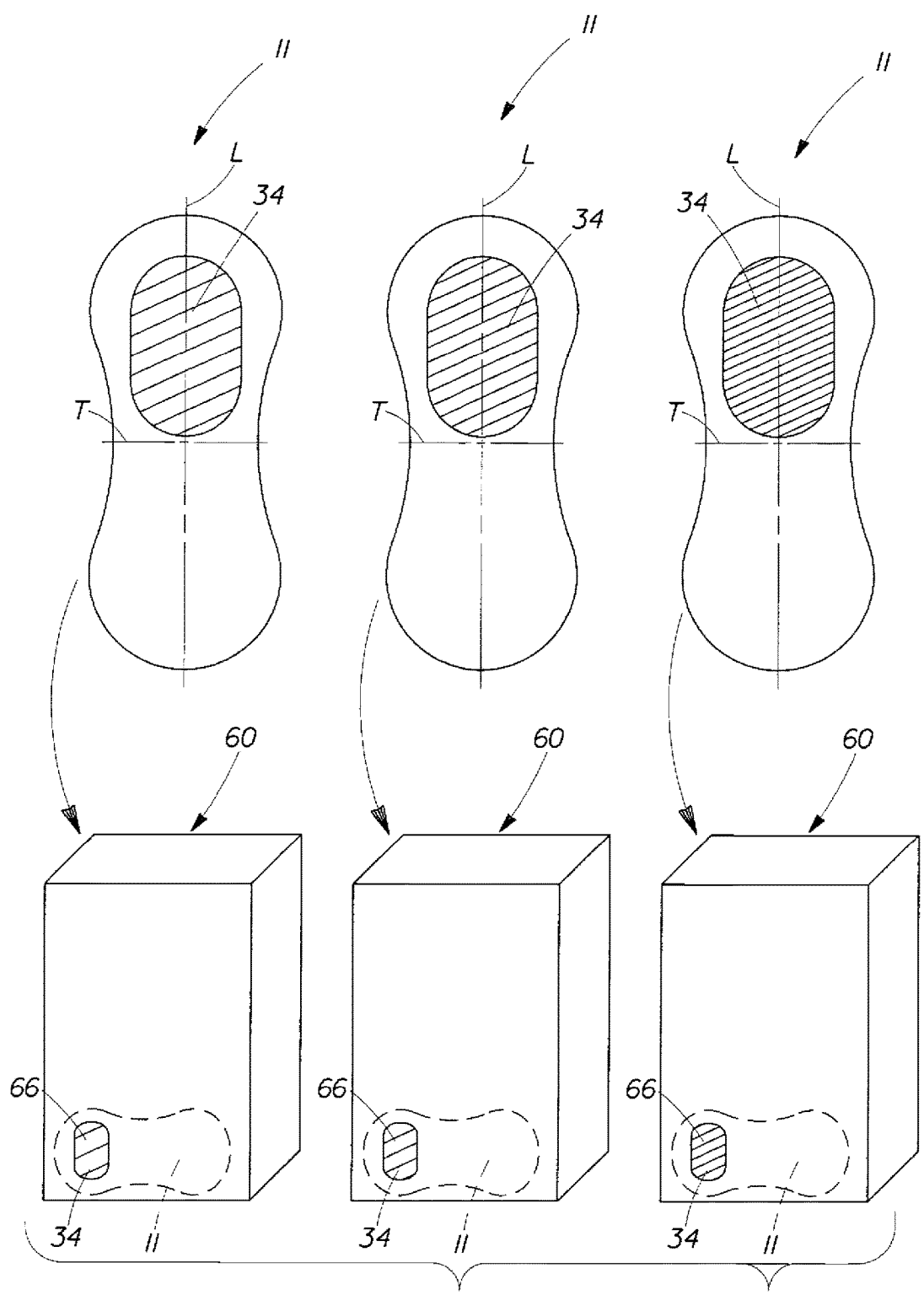
FIG. 13 is a view of an array of feminine hygiene articles and a corresponding array of packaging of the present invention.

In another embodiment, as shown in FIG. 13, an array 77 of packaging 60 can have at least one window or other substantially transparent opening 66 through which at least a portion of feminine hygiene articles such as sanitary napkins 11 inside packaging 60 can be seen. Window 66 (or windows 66 if two or more are present) can be a cutout portion of packaging 60 or a cutout having a transparent polymeric covering, or any other means known in the art to facilitate visual identification of functional enhancement indicator 34 of articles packaged inside otherwise opaque packaging. In one embodiment, feminine hygiene articles can be individually folded and/or packaged in individual wrappers prior to packaging in an array 77 of packages 60. In such embodiments, a corresponding visual indicator can be utilized on other portions of feminine hygiene articles or individual wrappers as necessary to indicate an array of functional characteristics through window 66.

Figure 14:
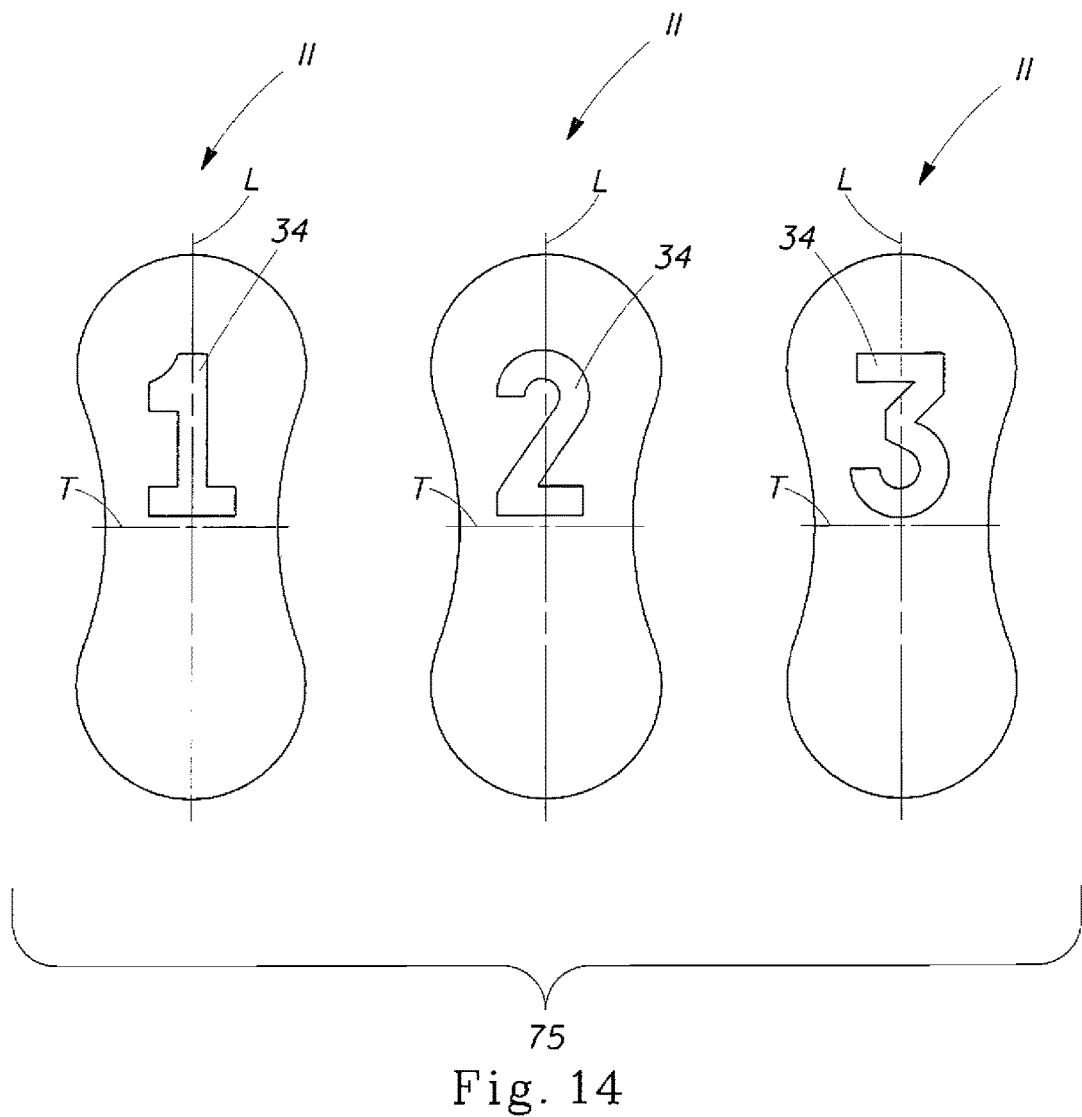
FIG. 14 is a view of an array of feminine hygiene articles of the present invention.

In another embodiment, feminine hygiene articles, such as sanitary napkins 11, can have functional enhancement indicators 34 that provide direct information-bearing signals to the user, such as numerals or written indicia that communicate information by way of clearly understood gradations in scale. For example, as shown in FIG. 14, an array 75 of sanitary napkins 11 can be identified by a number, with increasing numbers indicating an increase in a functional characteristic. For example, increasing numbers can signal an increasing amount of absorbent capacity relative to lower-numbered articles. As shown in FIG. 14, for example, the article on the far right numbered with the numeral "3" can have more absorbent capacity than that of the article in the middle numbered with the numeral "2". Other functional enhancement indicators 34 could be used for a more aesthetic appearance. As disclosed earlier, a plurality of sanitary napkins 11 can be sold in the same package, with the functional enhancement indicator 34 aiding the user in choosing a particular sanitary napkin for a given personal circumstance.

Note that in some embodiments, such as the embodiment shown in FIG. 14, it is not necessary that functional enhancement indicators 34 be closer to one end of the article than the other. While shown that way in FIG. 14, the benefit of the functional enhancement indicators 34 shown would be the same if the functional enhancement indicators 34 were centered with respect to both the longitudinal and transverse centerlines. Note also, functional enhancement indicators 34 that provide direct information-bearing signals to the user, such as numerals or written indicia that communicate information by way of clearly understood gradations in scale can also function to facilitate proper orientation of the article in the undergarment of the wearer due to the inherent uprightness associated with many such signals. Thus, the user would orient the middle pad of FIG. 14 with the "2" oriented with the top to the front of the pad.

Figure 15:
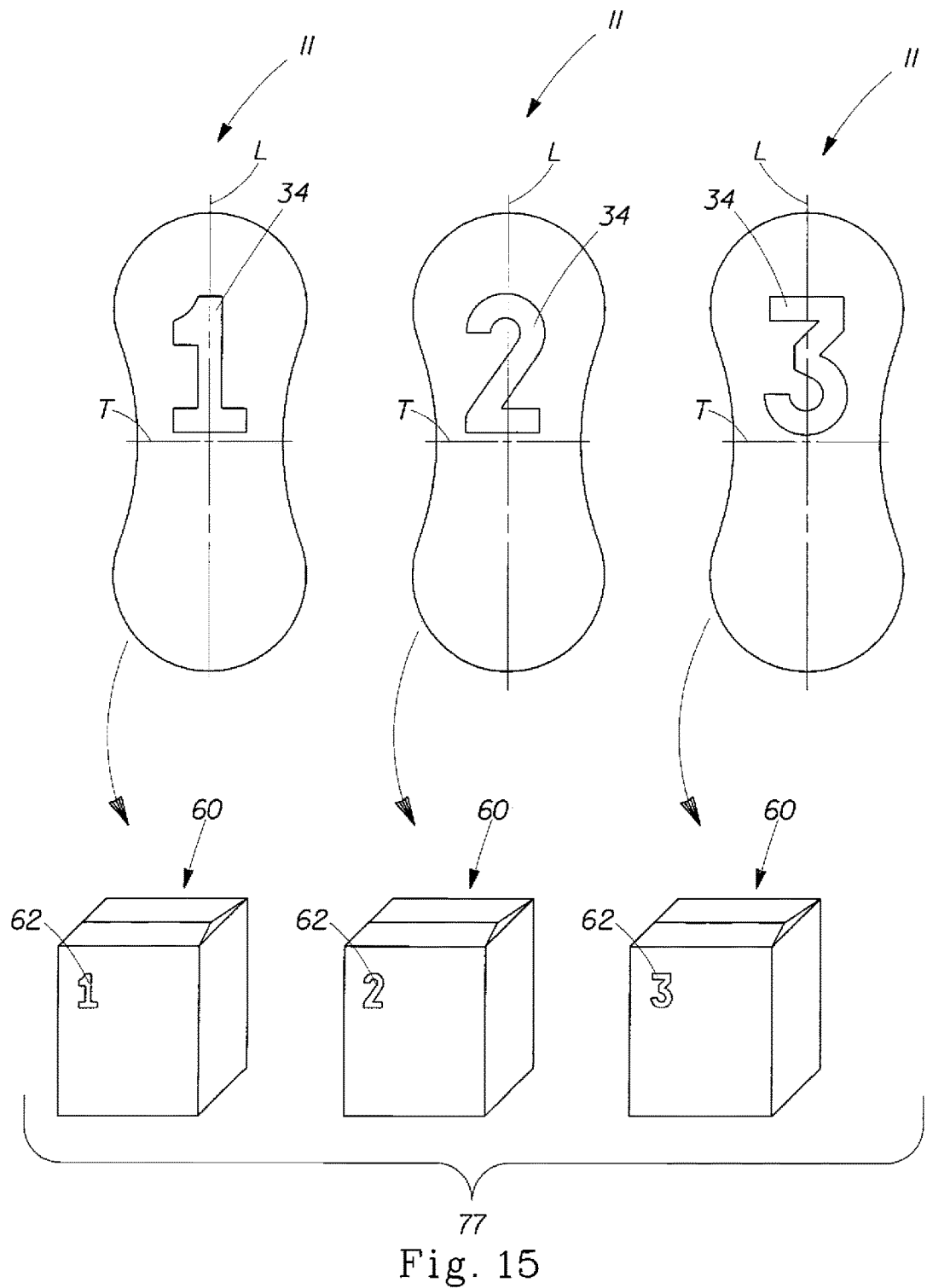
FIG. 15 is a view of an array of feminine hygiene articles and a corresponding array of packaging of the present invention.

Feminine hygiene articles providing direct information-bearing signals to the user can be packaged in an array of containers such as bags, boxes, or cartons, which carry similar information-bearing signals to aid a user in choosing an appropriate pad for an appropriate function. For example, as shown in FIG. 15, the sanitary napkins described in FIG. 14 can be packaged in an array 77 of poly bags 60 bearing a visual indicator 62 that corresponds in visual distinction to functional enhancement indicator 34. Thus, if functional enhancement indicator 34 is a numeral, visual indicator 62 can be a matching numeral. Thus, a consumer or user of feminine hygiene articles can choose a feminine hygiene article having a desired functional characteristic more easily based on the packaging, with a confirmation or reinforcement of that functional characteristic on each pad inside the packaging. Packaging can be transparent, at least in portions, such that the functional enhancement indicator 34 on one of the pads shows through the packaging to serve as both the functional enhancement indicator 34 and the visual indicator 62.

Figure 16:
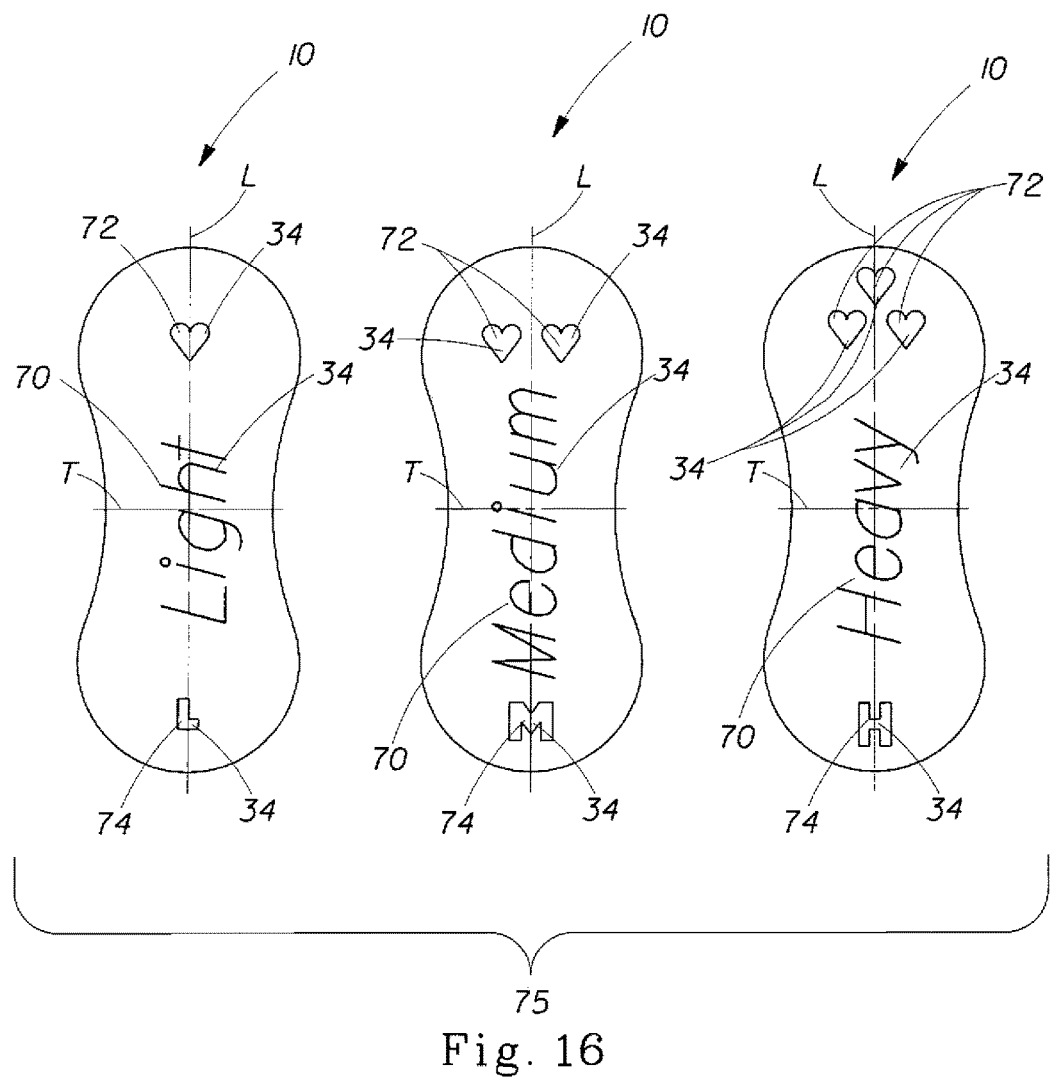
FIG. 16 is a view of an array of feminine hygiene articles of the present invention.

FIG. 16 shows an array 75 of incontinence pads 10 having a plurality of functional enhancement indicators 34. As shown, each pad 10 can have information-bearing written indicia 70 to literally "spell out" the functional characteristic, such as light urine capacity, medium urine capacity, or heavy urine capacity. In addition, or separately, an array of pads can be differentiated by the number of visually distinct pattern elements 72 such as the heart shapes shown in FIG. 16. Thus, the greater number of hearts, the greater the characteristic signaled by the functional enhancement indicator 34. In addition, or separately, the functional enhancement indicator 34 can include a shortened form of the information-bearing written indicia 74, such as "L" for light urine capacity, and the like.

In each case of the embodiments of the present invention shown in FIGS. 11-16, one benefit to the user is the identification in an array of products of differing functional characteristics, the product or products the user can choose for her particular needs. Further, another benefit to the user is the ability to take visual notice after use of a product to identify the product for future use. Thus, a user may use the middle pad shown in FIG. 16, for example, and find that it is perfect for her needs. Upon removing the pad she has direct visual reinforcement as to which pad of all the various kinds it is. This enables her to easily replace it with a like pad without having to remember what kind of pad she used. For this reason, it may be desirable to place functional enhancement indicators 34 near the pad periphery, such as pattern elements 72 or written indicia 74, such that the fluid absorbed in the pad during use does not alter or mask the indicator.

Figure 17:
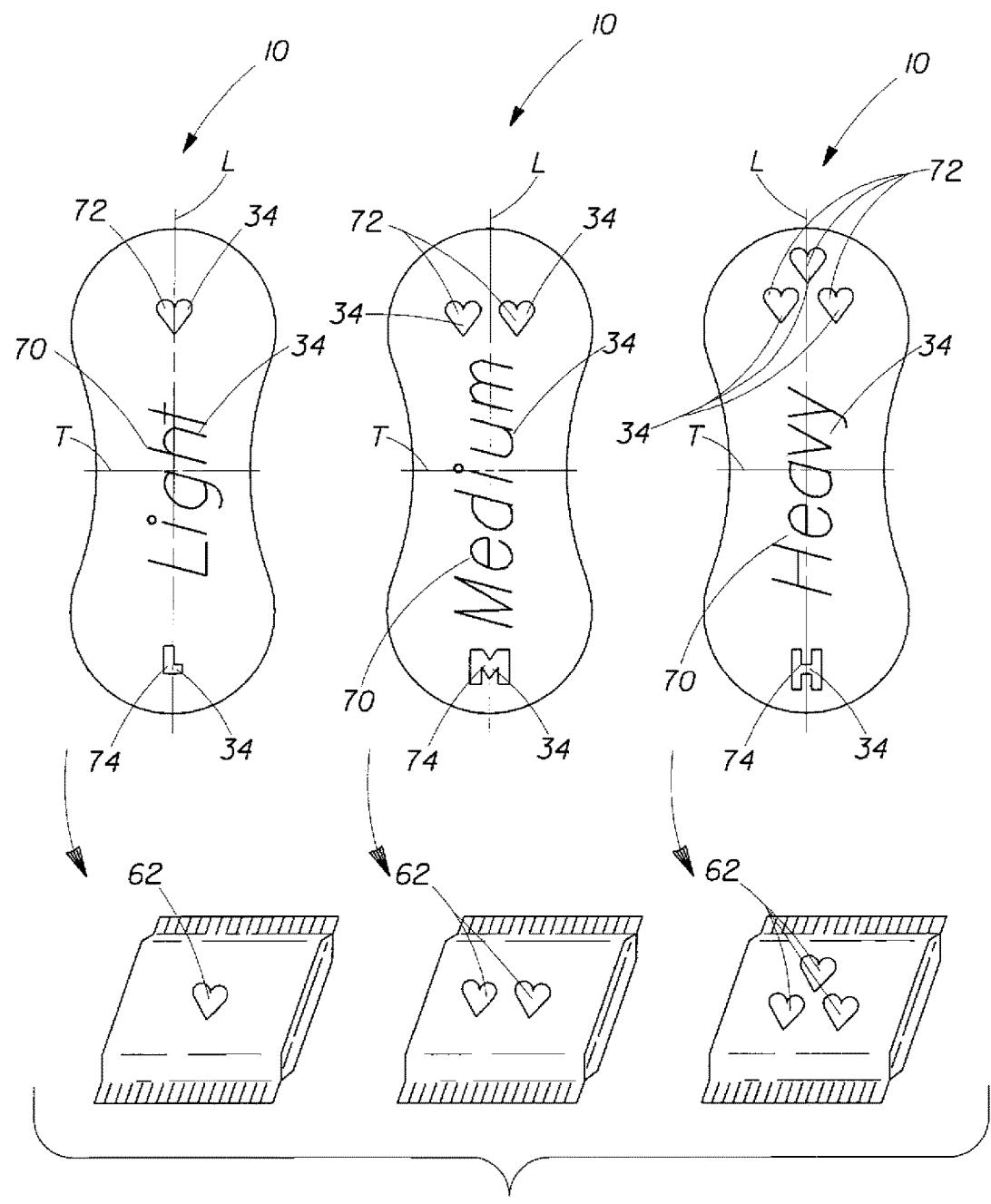
FIG. 17 is a view of an array of feminine hygiene articles and a corresponding array of packaging of the present invention.

Again, with respect to the pads shown in FIG. 16, each incontinence pad 10 can be individually packaged in an array 77 of flexible poly wrappers as shown in FIG. 17. The wrapper, and if so packaged, the box or bag of individually wrapped pads, can be identified by a corresponding visual signal 62 for one or more of the functional enhancement indicators 34. As shown in FIG. 17, each pad can be tri-folded and wrapped in a flexible wrapper that can also function as the release paper for the panty-fastening adhesive on the pad, as is known in the art. The wrapper can have thereon in a visually-distinct manner, such as by printing, a visual signal 62 corresponding to one or more of the functional enhancement indicators 34, such as the distinct heart-shaped pattern element 72.

Many variations on the above-described functional enhancement indicators are contemplated. For example, functional enhancement indicators can comprise sensory perception agents, such as menthol lactate in a sufficient amount so as to give the user a feeling of cooling refreshment when the incontinence pad is properly placed and worn. The functional enhancement indicators can be made such that, rather than printing with ink, a material is modified so as to have a different reflective index, or even be transparent, in the region intended to be a functional enhancement indicator. Likewise, instead of ink, color can be added by adding colored material in appropriate places, the colored material being additional film, nonwovens, or adhesives, including glue and hot melt adhesives. Such color can be added in or on any component of the feminine hygiene article, as long as it is visible to the user when she is positioning the incontinence pad in her undergarment.

In one embodiment a disposable feminine hygiene article of the present invention can be packaged either singly or in a package with other disposable absorbent articles such as other absorbent pads or tampons. The package can be labeled as to the intended use, as well as instructions for use, i.e., a method of properly placing and positioning the feminine hygiene article into the undergarment.

To aid the user in properly positioning feminine hygiene articles such as incontinence pads having functional enhancement indicators, that is, to aid the user in using the functional enhancement indicators as an orientation guide, the feminine hygiene article can be provided with instructions for use. Instructions for use can be provided on or in the packaging in which the feminine hygiene article is sold, on related advertising or display media, or on the feminine hygiene article itself. The instructions can be printed on packaging, such as on an outside surface thereof, or on a separate paper placed inside the packaging. A package can comprise a plurality of feminine hygiene articles, and each feminine hygiene article can be individually wrapped or packaged, as is commonly known in the art. Instructions for use can include indicia such as text and pictorial diagrams. The printed instructions can include instructions for choosing a feminine hygiene article of the present invention based on the size of the user's undergarment, the user's flow requirements, the user's age or weight, or any other criteria useful for choosing an effective feminine hygiene article.

A feminine hygiene article of the present invention can be used by following the method herein described. First, if there is a choice of feminine hygiene articles differentiated by intended use, such as menstrual use or incontinence use, the user can choose one or the other. The user can choose the feminine hygiene article having the functionally enhanced characteristics desired, possibly from an array of products differentiated in the enhanced functional characteristic. In another embodiment, the user can choose by reference to a use guide posted on a plainly visible sign or banner showing various choices in feminine protection and corresponding functional enhancement indicators or visual signals corresponding to the users needs. In one embodiment the use guide can be made available electronically, such as via the internet. One the user has chosen and obtained her feminine hygiene article, the following method steps are followed.

It is preferred that the user place the feminine hygiene article into her undergarment while the undergarment is being worn, but pulled down about her legs such that the crotch portion thereof is visible and accessible. The user can then remove one feminine hygiene article from its packaging, including any individual wrappers, if any. If the feminine hygiene article is provided with pressure sensitive adhesive attachment means, the user can remove any backing strips, release paper, or other covering to expose the adhesive.

Once the feminine hygiene article is unwrapped, unfolded, or otherwise prepared for placement, the user can observe the functional enhancement indicator(s) provided thereon and visibly-distinct from the body-facing surface thereof, and prepare to place the feminine hygiene article in her undergarment while spreading the crotch portion thereof with her legs. She can then place the feminine hygiene article in her panty, noting the placement of the functionally-enhanced region if necessary. Thus, for an asymmetrically-shaped incontinence pad (such as shown in FIG. 1), the user can use the functional enhancement indicator markings on one end thereof to orient the wider end of the pad toward the front of her undergarment.

Placement can be achieved by known methods, such as by exposing (such as by removing a release paper) pressure sensitive adhesive on the garment-facing side of the feminine hygiene article, and pressing the feminine hygiene article into the crotch portion of her undergarment.

After placement, the user can check for proper positioning, and, if necessary, remove and replace the feminine hygiene article for better alignment. This step can be repeated as necessary.

If the feminine hygiene article is provided with flaps, the user can then fold the flaps down and under the crotch portion of the undergarment, and, if provided for, affix the flaps to the undergarment by means provided, such as by adhesive attachment means.

The user can then pull up her undergarment, assured that the feminine hygiene article is properly placed for optimal functioning while minimizing product misplacement that can lead to garment soiling.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a body-facing surface, a garment-facing surface, a first end region a second end region, a topsheet, a backsheet, and an absorbent core disposed between the topsheet and the backsheet, and panty fastening adhesive disposed on the garment-facing surface, and the absorbent article further comprising:
   a) a first functional enhancement indicator that is that is only visually perceptible from the body-facing surface; and
   b) a second functional enhancement indicator that is both visually and tactilely perceptible from the body-facing surface, wherein the second functional enhancement indicator provides an indication of a region of enhanced fluid containment, wherein the second functional enhancement indicator is disposed on a surface below the topsheet, and wherein the tactile perception of the second functional enhancement indicator is not from an embossment.

2. The absorbent article of claim 1, wherein the first functional enhancement indicator is printed on the topsheet.

3. The absorbent article of claim 1, wherein the absorbent article further comprises a secondary topsheet, and wherein the first functional enhancement indicator is printed on the secondary topsheet.

4. The absorbent article of claim 1, wherein the first functional enhancement indicator is off-center with respect to a transverse centerline of the absorbent article.

5. The absorbent article of claim 4, wherein the second functional enhancement indicator is off-center with respect to the transverse centerline of the absorbent article.

6. The absorbent article of claim 1, wherein the second functional enhancement indicator is off-center with respect to a transverse centerline of the absorbent article.

* * * * *